(12) United States Patent
Fliri et al.

(10) Patent No.: US 9,670,175 B2
(45) Date of Patent: Jun. 6, 2017

(54) PROTECTED SUCCINATES FOR ENHANCING MITOCHONDRIAL ATP-PRODUCTION

(71) Applicant: NEUROVIVE PHARMACEUTICALS AB, Lund (SE)

(72) Inventors: Hans Georg Fliri, Ongar (GB); Rhonan Lee Ford, Ongar (GB); David Arthur Scowen, Ongar (GB); Derek Gregory Batcheller, Lund (SE); Kari Henrik Johannes Ehinger, Lund (SE); Mats Eskil Elmer, Lund (SE); Magnus Joakim Hansson, Lund (SE); Karl Fredrik Lennart Sjovall, Lund (SE)

(73) Assignee: NEUROVIVE PHARMACEUTICALS AB, Lund (SE)

( * ) Notice: Subject to any disclaimer, the term of this patent is extended or adjusted under 35 U.S.C. 154(b) by 0 days.

(21) Appl. No.: 14/433,558

(22) PCT Filed: Oct. 4, 2013

(86) PCT No.: PCT/GB2013/052598
§ 371 (c)(1),
(2) Date: Apr. 3, 2015

(87) PCT Pub. No.: WO2014/053857
PCT Pub. Date: Apr. 10, 2014

(65) Prior Publication Data
US 2015/0259317 A1 Sep. 17, 2015

(30) Foreign Application Priority Data

Oct. 5, 2012 (GB) .................................. 1217823.2
Jun. 19, 2013 (GB) .................................. 1310925.1

(51) Int. Cl.
| | | |
|---|---|---|
| A01N 43/26 | (2006.01) |
| A61K 31/335 | (2006.01) |
| C07C 69/34 | (2006.01) |
| C07C 69/52 | (2006.01) |
| C07D 317/34 | (2006.01) |
| C07C 69/40 | (2006.01) |
| C07C 69/708 | (2006.01) |
| C07D 323/00 | (2006.01) |
| C07C 235/06 | (2006.01) |

(52) U.S. Cl.
CPC ............ *C07D 317/34* (2013.01); *C07C 69/40* (2013.01); *C07C 69/708* (2013.01); *C07C 235/06* (2013.01); *C07D 323/00* (2013.01)

(58) Field of Classification Search
USPC ......................................... 514/467; 560/190
See application file for complete search history.

(56) References Cited

U.S. PATENT DOCUMENTS 6,054,591 A * 4/2000 Aono .................. A61K 31/415
548/319.1

FOREIGN PATENT DOCUMENTS

| WO | 97/47584 A1 | 12/1997 |
| WO | 02/28345 A2 | 4/2002 |
| WO | 2009/019534 A2 | 2/2009 |

OTHER PUBLICATIONS

Robinson et. al. (J. Med. Chem. (1996) 39:10-18).*

(Continued)

*Primary Examiner* — Marcos Sznaidman
(74) *Attorney, Agent, or Firm* — Foley & Lardner LLP

(57) ABSTRACT

Disclosed herein are mono or di-succinate compounds where one or both of the acid groups in the succinate core are protected in the form of biologically labile moieties, and the use of said compounds to enhance mitochondrial function. The compounds may be of formula (I) wherein $R_1$ is H or an optionally substituted alkyl group or a group of formula (II) and $R_2$ is independently a group according to formula (II) where formula (II) is as defined 10 herein.

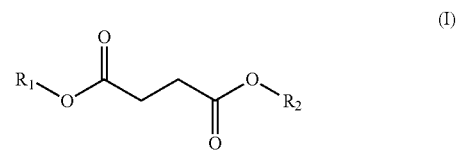

(I)

2 Claims, 3 Drawing Sheets

(56) References Cited

OTHER PUBLICATIONS

Ito et al., "Subchronic and chronic toxicity of a new REM sleep-inducing hypnotic, calcium N-(2-ethylhexyl)-2-hydroxylbutyramide semisuccinate ester salt (M-2)" J. Med. Soc. Toho, Japan, vol. 17(5-6): 531-542, 1970 (Chem. Abs. No. 75:3844).

Nudelman et al., "The Role of Intracellularly Released Formaldehyde and Butyric Acid in the Anticancer Activity of Acyloxyalkyl Esters" J. Med. Chem., vol. 48(4):1042-1054, 2005.

Rephaeli et al., "The selectivity and anti-metastic activity of oral bioavailable butyric acid prodrugs" Investigational New Drugs, vol. 24(5): 383-392, 2006.

International Search Report and Written Opinion; PCT/GB2013/052598, mailed Nov. 22, 2013.

Robinson et al., "Discovery of the Hemifumarate and (.alpha.-L-alanyloxy)methyl ether as prodrugs of antirheumatic oxindole: Prodrugs for the enolic OH group" J. Med. Chem. Am. Chem Soc. US, vol. 39(1):10-18, Jan. 1, 1996.

Noel et al. "Synthesis and biological properties of conjugates betweenfluoroquinolones and a N3"-functionalized pyochelin" Org. and Biom. Chem., vol. 9:8288-8300, 2011.

Roy et al., "Design and synthesis of enediyne-based peptide with selective peptide-cleaving activity" Chemical Communications, vol. 46:2283-2285, 2010.

\* cited by examiner

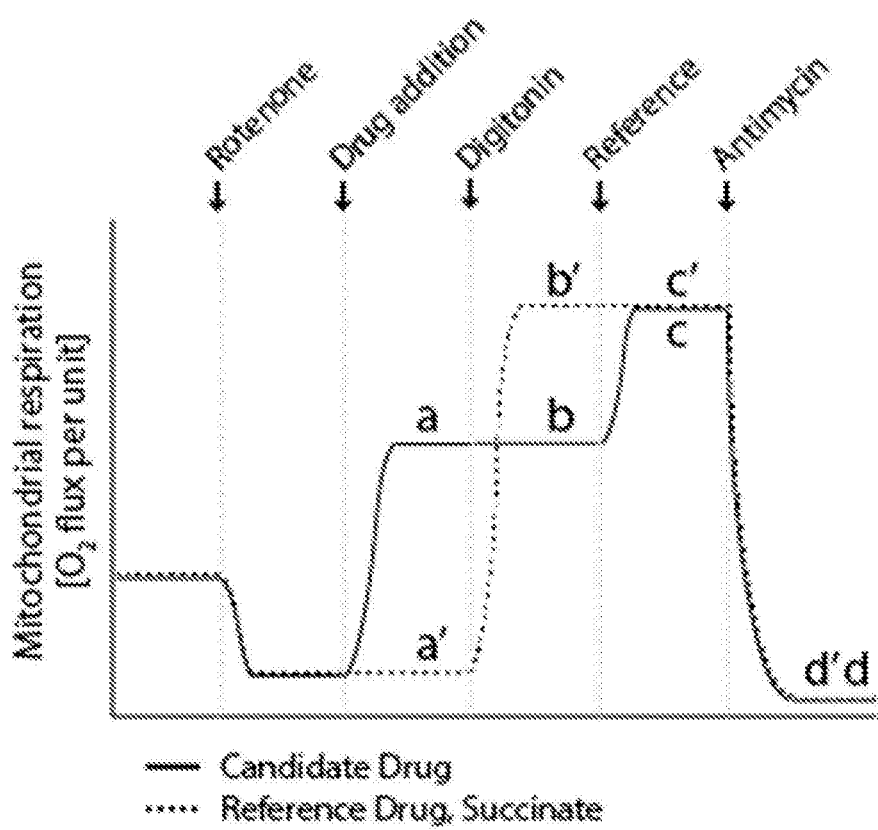
Fig 1. Schematic figure of mitochondrial complex II screening assay.

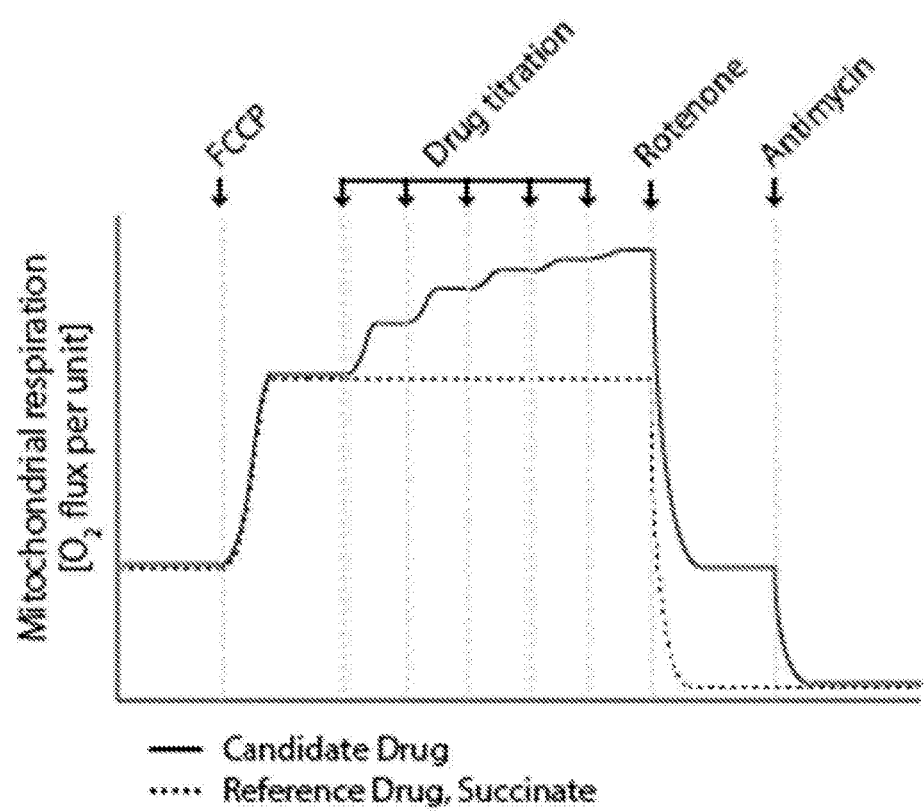
Fig 2. Schematic figure of mitochondrial convergent respiration screening assay.

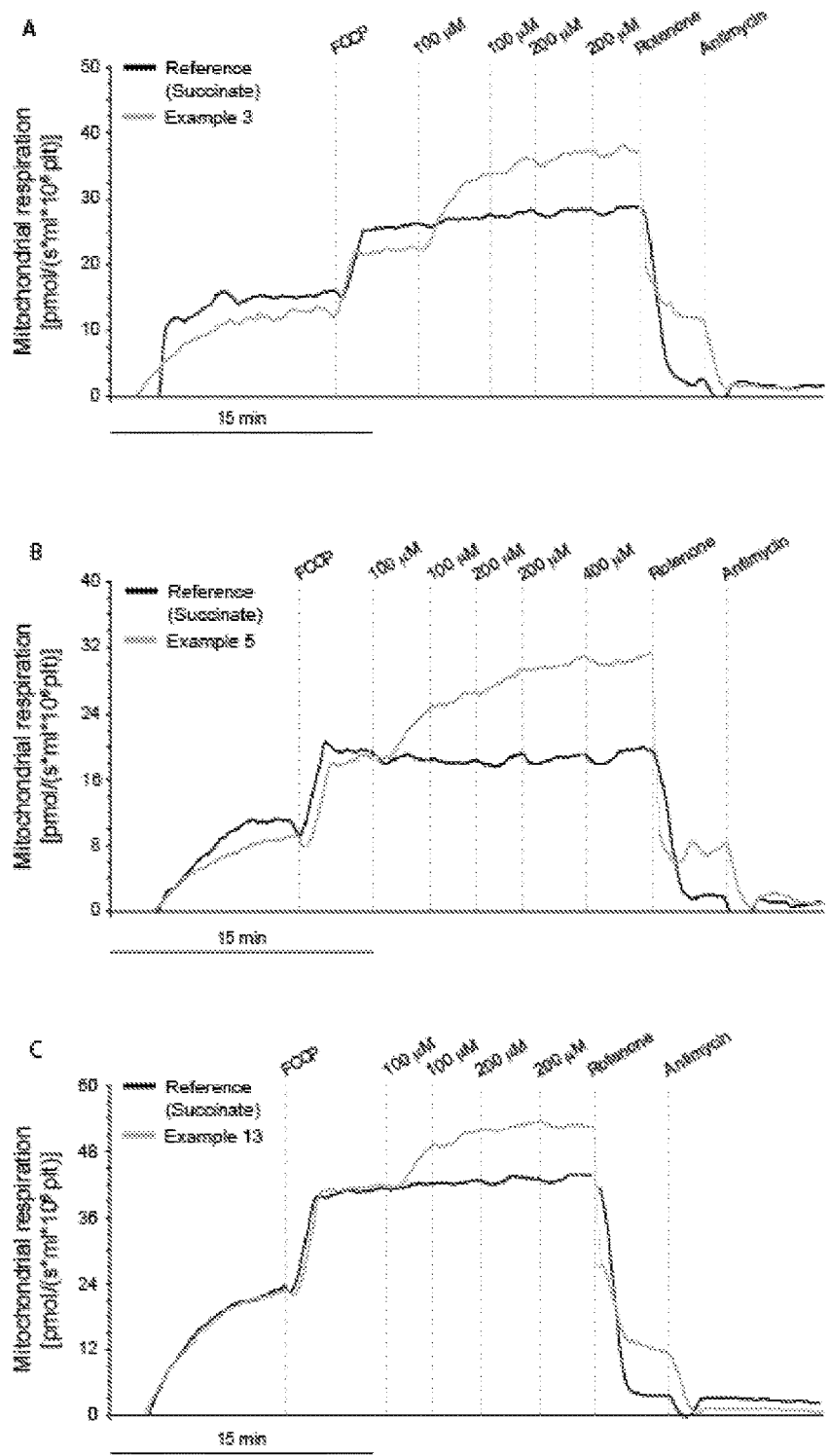
Fig 3. Exemplifying experimental traces for convergent mitochondrial respiration [pmol/(s*ml*10⁶plt)]

PROTECTED SUCCINATES FOR ENHANCING MITOCHONDRIAL ATP-PRODUCTION

CROSS-REFERENCE TO RELATED APPLICATIONS

This application is a 35 U.S.C. §371 national stage filing of International Application No. PCT/GB2013/052598, filed on Oct. 4, 2013, which claims the benefit of United Kingdom Patent Application Nos. 1217823.2, filed on Oct. 5, 2012, and 1310925.1, filed on Jun. 19, 2013. Each of the foregoing applications is incorporated herein by reference in its entirety.

FIELD OF THE INVENTION

The present invention provides novel protected succinates for enhancing ATP-production in mitochondria. The main part of ATP produced and utilized in the eukaryotic cell originates from mitochondrial oxidative phosphorylation, a process to which high-energy electrons are provided by the Kreb's cycle. Not all Kreb's cycle intermediates are readily permeable to the cellular membrane, one of them being succinate. The provision of the novel protected succinates is envisaged to allow passage over the cellular membrane and thus the protected succinates can be used to enhance mitochondrial ATP-output.

The present invention also provides methods for preparing the novel protected succinates as well as their use in medicine and/or in cosmetics. Notably, the protected succinates are useful in the prevention or treatment of mitochondria-related disorders, in maintaining normal mitochondria function, or in restoring defects in the mitochondrial respiratory system.

BACKGROUND OF THE INVENTION

Mitochondria are organelles in eukaryotic cells. They generate most of the cell's supply of adenosine triphosphate (ATP), which is used as an energy source. Thus, mitochondria are indispensable for energy production, for the survival of eukaryotic cells and for correct cellular function. In addition to supplying energy, mitochondria are involved in a number of other processes such as cell signalling, cellular differentiation, cell death as well as the control of the cell cycle and cell growth. In particular, mitochondria are crucial regulators of cell apoptosis and they also play a major role in multiple forms of non-apoptotic cell death such as necrosis.

In recent years many papers have been published describing mitochondrial contributions to a variety of diseases. Some diseases may be caused by mutations or deletions in the mitochondrial genome, while others may be caused by impairment of the mitochondrial respiratory system or other kind of damage of the mitochondrial function. At present there is no available treatment that can cure mitochondrial diseases.

In view of the recognized importance of maintaining or restoring a normal mitochondrial function or of enhancing the cell's energy production (ATP), there is a need to develop compounds, which have these properties.

Succinate compounds have been prepared as prodrugs of other active agents, for example WO0208345 describes succinic acid bis(2,2-dimethylpropionyloxymethyl) ester, succinic acid dibutyryloxymethyl ester and succinic acid bis-(1-butyryloxy-ethyl)ester. These compounds are prepared as agents to deliver formaldehyde, and are aimed at different medical uses to the current compounds.

Prior art compounds include WO9747584, which describes a range of polyol succinates.

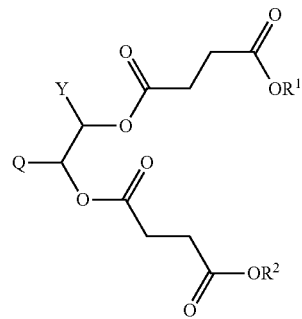

In the example given therein, Y is an H or alkyl group. Each succinate compound contains multiple succinate moieties linked by a group of structure C(Y)—C(Q), and each ester acid is therefore directly linked to a moiety containing at least two carbon atoms in the form of an ethyl group O—C—C. Each compound disclosed contains more than one succinate moiety, and the succinate moiety is not protected by a moiety of type O—C—X where X is a heteroatom.

Various succinate ester compounds are known in the art. Diethyl succinate, monomethyl succinate and dimethyl succinate are shown to be inactive in the assays exemplified below, and fall outside the scope of the invention.

SUMMARY OF THE INVENTION

Disclosed herein are mono or di-succinate compounds where one or both of the acid groups in the succinate core are protected in the form of biologically labile moieties. Disclosed herein is a protected succinate of formula (I)

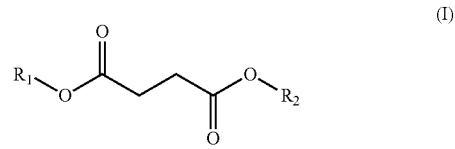

wherein $R_1$ is H or a pharmaceutically acceptable salt, or an optionally substituted alkyl group or a group of formula (II) and $R_2$ is independently a group according to formula (II) where formula (II) is

wherein $R_3$ and $R_4$ are independently H, optionally substituted $C_1$-$C_3$ alkyl, or are linked together to form a ring and where $R_5$ is linked to $R_1$ to form a ring or $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl or optionally substituted cycloalkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring and wherein the compound is not succinic acid bis(2,2-dimethylpropionyloxymethyl) ester; succinic acid dibutyryloxymethyl ester; or succinic acid bis-(1-butyryloxy-ethyl) ester.

Disclosed herein is a protected succinate of formula (I)

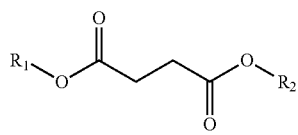

(I)

wherein $R_1$ is H, a pharmaceutically acceptable salt, an optionally substituted alkyl group or a group of formula (II) and $R_2$ is independently a group according to formula (II) where formula (II) is

(II)

wherein $R_3$ is H, optionally substituted $C_1$-$C_3$ alkyl, or is linked together with $R_5$ by a group of formula COO (CR'R")O to form a ring, where R' and R" are independently H, optionally substituted $C_1$-$C_3$ alkyl, or are linked together to form a ring;

$R_4$ is H;

$R_5$ is $OCOR_a$, $OCOOR_b$, $OCONR_cR_d$, $SO_2R_e$, $OPO(OR_f)(OR_g)$, $CONR_cR_d$ or is linked to $R_3$ by a group of formula COO(CR'R")O to form a ring, where R' and R" are independently H, optionally substituted $C_1$-$C_3$ alkyl, or are linked together to form a ring; where $R_a$ is optionally substituted methyl, ethyl or cycloalkyl;

$R_b$ is optionally substituted $C_1$-$C_3$ alkyl;

$R_c$ and $R_d$ are independently H, optionally substituted alkyl or are linked together to form a ring which may contain one or more further heteroatoms; $R_e$ is optionally substituted alkyl; and $R_f$ and $R_g$ are independently, H, methyl, ethyl or are linked together to form a ring.

In certain examples of the compounds, $R_3$ and/or $R_4$ can be methyl or ethyl. $R_3$ can be methoxy or ethoxy.

In certain examples of the compounds, $R_1$ can be methyl.

In certain examples of the compounds $R_5$ can be an optionally substituted alkyl ester providing the alkyl ester does not contain a further succinate ($OCOCH_2CH_2COO$) moiety. $R_5$ can be $OCOR_a$ where $R_a$ is $CH_3$, $CH_2CH_3$, $CH(CH_3)_2$.

The compound can be where $R_1$ and $R_5$ are linked together to form a ring and the ring comprises one or more acetal groups. Compounds may include those according to formula (III)

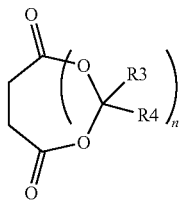

(III)

where $R_3$ and $R_4$ are independently H, optionally substituted $C_1$-$C_3$ alkyl, or are linked together to form a ring and n is 1-3.

The compound can be of type

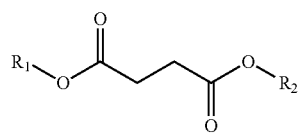

(I)

wherein $R_1$ is H or an optionally substituted alkyl group or a group of formula (II) and $R_2$ is independently a group according to formula (II) where formula (II) is

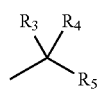

(II)

wherein $R_3$ and $R_4$ are independently H, optionally substituted $C_1$-$C_3$ alkyl, or are linked together to form a ring and $R_5$ is selected from $OCONR_cR_d$ or $CONR_cR_d$ where $R_c$ and $R_d$ are independently H, optionally substituted alkyl or are linked together to form a ring which may contain one or more further heteroatoms. In such cases $R_c$ and $R_d$ can be methyl or ethyl.

The compound can be of type (I)

where $R_1$ is H or an optionally substituted alkyl group or a group of formula (II) and $R_2$ is independently a group according to formula (II) where formula (II) is (II)

wherein $R_3$ and $R_5$ are linked together to form a ring and the ring comprises a moiety of formula (V) where formula (V) is

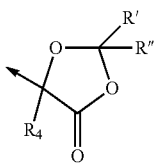

(V)

wherein $R_4$ is H or optionally substituted $C_1$-$C_3$ alkyl and R' and R" are independently H, optionally substituted $C_1$-$C_3$ alkyl, or are linked together to form a ring.

The compound may be a compound according to formula (Va) where formula (Va) is

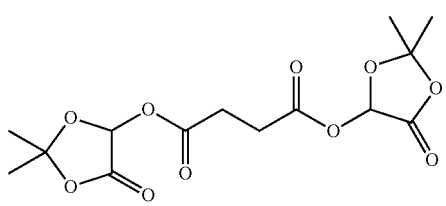

(Va)

The compound may be a compound according to formula XI where formula XI is

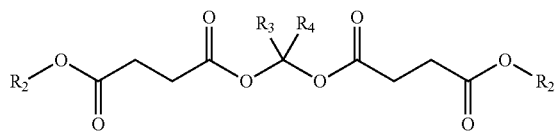

(XI)

wherein $R_3$ and $R_4$ are independently H, optionally substituted $C_1$-$C_3$ alkyl, or are linked together to form a ring and each $R_2$ may be independently a group according to formula (II) where formula (II) is

(II)

wherein $R_3$ is H, optionally substituted $C_1$-$C_3$ alkyl, or is linked together with $R_5$ by a group of formula COO(CR'R")O to form a ring, where R' and R" are independently H, optionally substituted $C_1$-$C_3$ alkyl, or are linked together to form a ring;
$R_4$ is H;
$R_5$ is $OCOR_a$, $OCOOR_b$, $OCONR_cR_d$, $SO_2R_e$, $OPO(OR_f)(OR_g)$, $CONR_cR_d$ or is linked to $R_3$ by a group of formula COO(CR'R")O to form a ring, where R' and R" are independently H, optionally substituted $C_1$-$C_3$ alkyl, or are linked together to form a ring; where
$R_a$ is optionally substituted methyl, ethyl or cycloalkyl;
$R_b$ is optionally substituted $C_1$-$C_3$ alkyl;
$R_c$ and $R_d$ are independently H, optionally substituted alkyl or are linked together to form a ring which may contain one or more further heteroatoms; $R_e$ is optionally substituted alkyl; and $R_f$ and $R_g$ are independently, H, methyl, ethyl or are linked together to form a ring.

The compound may be selected from

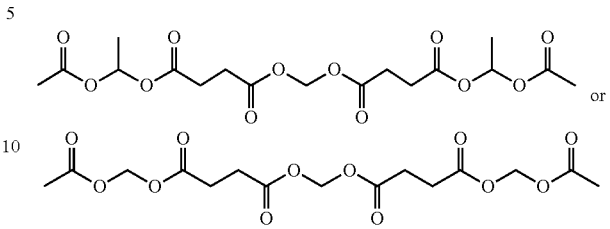

or

The compound may be a compound according to formula XII where formula XII is

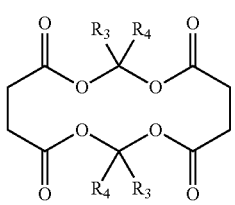

(XII)

wherein $R_3$ and $R_4$ are independently H, optionally substituted $C_1$-$C_3$ alkyl, or are linked together to form a ring.

Compounds as described herein can be used in medicine or in cosmetics, or in the manufacture of a composition for such use. The medicament can be used in the treatment of metabolic diseases, or in the treatment of diseases of mitochondrial dysfunction, treating or suppressing of mitochondrial disorders. The compounds may be used in the stimulation of mitochondrial energy production. The compounds may be used in the treatment of cancer and following hypoxia, ischemia, stroke, myocardial infarction, acute angina, an acute kidney injury, coronary occlusion and atrial fibrillation, or to avoid or counteract reperfusion injuries.

BRIEF DESCRIPTION OF THE DRAWINGS

FIG. 1 is a schematic figure of mitochondrial complex II screening assay. It shows the protocol for evaluating novel cell-permeable mitochondrial substrates. In the assay, mitochondrial function in intact cells is repressed with the respiratory complex I inhibitor rotenone. Drug candidates are compared with endogenous substrates (succinate) before and after permeabilization of the plasma membrane to evaluate bioenergetic enhancement or inhibition.

FIG. 2 is a schematic figure of mitochondrial convergent respiration screening assay. It describes the protocol for evaluating the potency of novel cell-permeable mitochondrial substrates. In the assay, mitochondrial activity is stimulated by uncoupling the mitochondria with the protonophore FCCP. Drug candidates are titrated to obtain the level of maximum convergent (complex I- and complex II-derived) respiration. After rotenone addition, complex II-dependent stimulation is obtained. The complex III-inhibitor antimycin is added to evaluate non mitochondrial oxygen consumption. The reference substance is succinate.

FIGS. 3A-3C show the increase in respiration (oxygen flux per unit) with stepwise titration of Example 3, 5, or 13 compared to a control (disodium succinate) in intact human platelets (assay described in FIG. 2).

DETAILED DESCRIPTION

Compounds according to the present invention can be used to enhance energy production in mitochondria. Notably the compounds can be used in medicine or in cosmetics. The compounds can be used in the prevention or treatment of disorders or diseases having a component relating to mitochondrial dysfunction.

Enhancement of energy production is e.g. relevant in subjects suffering from a mitochondrial defect, disorder or disease. Mitochondrial diseases result from dysfunction of the mitochondria, which are specialized compartments present in every cell of the body except red blood cells. When mitochondria fail, less and less energy is generated within the cell and cell injury or even cell death will follow. If this process is repeated throughout the body the life of the subject in whom this is happening is severely compromised.

Diseases of the mitochondria appear most often in organs that are very energy demanding such as the brain, heart, liver, skeletal muscles, kidney and the endocrine and respiratory system.

Symptoms of a mitochondrial disease may include loss of motor control, muscle weakness and pain, seizures, visual/hearing problems, cardiac diseases, liver diseases, gastrointestinal disorders, swallowing difficulties and more.

A mitochondrial disease may be inherited or may be due to spontaneous mutations, which lead to altered functions of the proteins or RNA molecules normally residing in the mitochondria.

Many diseases have been found to involve a mitochondrial deficiency such as a Complex I, II, III or IV deficiency or an enzyme deficiency like e.g. pyruvate dehydrogenase deficiency. However, the picture is complex and many factors may be involved in the diseases.

Up to now, no curative treatments are available. The only treatments available are such that can alleviate the symptoms and delay the progression of the disease. Accordingly, the findings by the present inventors and described herein are very important as they demonstrate the beneficial effect of the compounds of succinic acid on the energy production in the mitochondria.

Disclosed herein is a protected succinate of formula (I)

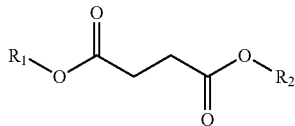

where $R_1$ is H or a pharmaceutically acceptable salt, or an optionally substituted alkyl group or a group of formula (II) and $R_2$ is independently a group according to formula (II) where formula (II) is

where $R_3$ and $R_4$ are independently H, optionally substituted $C_1$-$C_3$ alkyl, or are linked together to form a ring and where $R_5$ is linked to $R_1$ to form a ring or $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl with the exception of n-propyl ($CH_3CH_2CH_2$—), $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

$R_1$ and $R_2$ can be the same, or $R_1$ can be a different formula (II) such that both acids of the succinate are protected in the form of different moieties where $R_1$ and $R_2$ are different. In certain examples of the compounds, $R_1$ can be alkyl. $R_1$ can be methyl. $R_1$ can be ethyl. Both $R_1$ and $R_2$ can be different versions of formula (II) such that each end of the succinate molecule is provided with a different moiety.

In certain examples of the compounds, $R_3$ and/or $R_4$ can be methyl or ethyl. $R_3$ can be H. $R_3$ can be $C_1$-$C_3$ alkoxy, for example methoxy or ethoxy. $R_4$ can be H. If each end of the succinate are different versions of formula (II), then $R_3$ and $R_4$ can be different at each end of the succinate molecule. $R_3$ and $R_4$ can be linked together to form a ring. $R_3$ and $R_5$ can be linked together to form a ring. The ring may be an all carbon ring, or may contain additional heteroatoms. The $R_3$-$R_5$ ring may contain one or more OCR'R"O linkages where R' and R" are independently H, optionally substituted $C_1$-$C_3$ alkyl, or are linked together to form a ring. The compounds may be of formula:

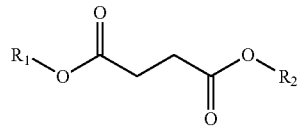

where $R_1$ is H or a pharmaceutically acceptable salt, or an optionally substituted alkyl group or a group of formula (II) and $R_2$ is independently a group according to formula (II) where formula (II) is

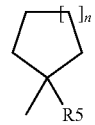

where n is 0-4 and $R_5$ is linked to $R_1$ to form a ring or $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

In certain examples of the compounds $R_5$ can be an optionally substituted alkyl ester providing the alkyl ester does not contain a further succinate ($O_2CCH_2CH_2CO_2$) moiety. $R_5$ can be an optionally substituted alkyl ester with the exception of butyl ester where $R_5$ is $OCOCH_2CH_2CH_3$. $R_5$ can be $OCOR_a$ where $R_a$ is $CH_3$, $CH_2CH_3$, $CH(CH_3)_2$ or $C(CH_3)_3$.

Exemplary compounds may be of formula

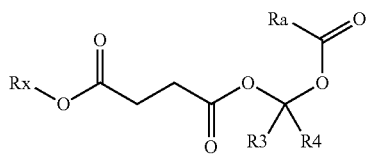

where $R_3$ and $R_4$ are independently H, optionally substituted $C_1$-$C_3$ alkyl, or are linked together to form a ring, Ra is $CH_3$, $CH_2CH_3$, $CH(CH_3)_2$ or $C(CH_3)_3$ and $R_x$ is H or a pharmaceutically acceptable salt or alkyl or an optionally substituted alkyl or a group of formula (II) where formula (II) is

where $R_3$ and $R_4$ are independently H, optionally substituted C1-C3 alkyl, or are linked together to form a ring and where $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

Exemplary compounds can be where $R_1$ and $R_5$ are linked together to form a ring and the ring comprises one or more acetal groups. Compounds may include those according to formula (III)

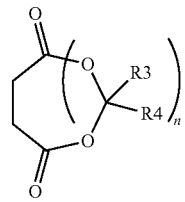

where $R_3$ and $R_4$ are independently H, optionally substituted $C_1$-$C_3$ alkyl, or are linked together to form a ring and n is 1-3. In certain examples of the compounds, $R_3$ and/or $R_4$ can be methyl or ethyl. $R_3$ can be H. $R_4$ can be H. If n is greater than 1, each of the $R_3$ and $R_4$ groups can be different at each acetal moiety. $R_3$ and $R_4$ can be linked together to form a ring. The ring may be an all carbon ring, or may contain additional heteroatoms. Examples where n is 1, 2 and 3 are shown below:

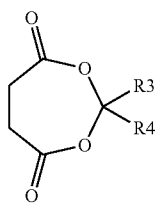 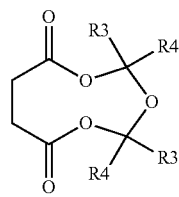

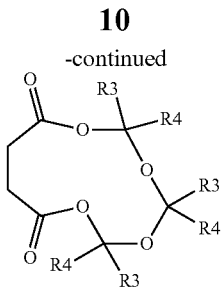

Exemplary compounds can be of type

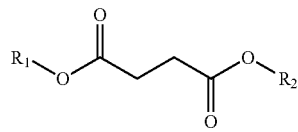

wherein $R_1$ is H or an optionally substituted alkyl group or a group of formula (II) and $R_2$ is independently a group according to formula (II) where formula (II) is

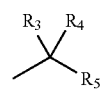

wherein $R_3$ and $R_4$ are independently H, optionally substituted $C_1$-$C_3$ alkyl, or are linked together to form a ring and $R_5$ is $OCOOR_b$ where $R_b$ is optionally substituted alkyl. In such cases $R_b$ can be alkyl. In such cases $R_b$ can be methyl or ethyl.

Exemplary compounds may be of formula

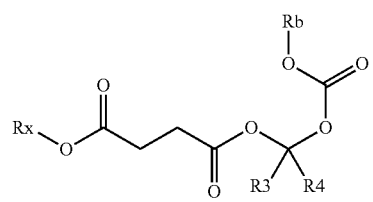

where $R_3$ and $R_4$ are independently H, optionally substituted $C_1$-$C_3$ alkyl, or are linked together to form a ring, $R_b$ is H, alkyl or optionally substituted alkyl and $R_x$ is H or a pharmaceutically acceptable salt or alkyl or optionally substituted alkyl or a group of formula (II) where formula (II) is

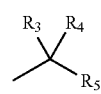

where $R_3$ and $R_4$ are independently H, optionally substituted $C_1$-$C_3$ alkyl, or are linked together to form a ring and where $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring. In such cases $R_b$ can be alkyl. In such cases $R_b$ can be methyl or ethyl.

Exemplary compounds can be of type

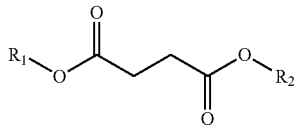

wherein $R_1$ is H or an optionally substituted alkyl group or a group of formula (II) and $R_2$ is independently a group according to formula (II) where formula (II) is

where $R_3$ is linked together with $R_5$ by a group of formula COO(CR'R")O to form a ring, where R' and R" are independently H, optionally substituted $C_1$-$C_3$ alkyl, or are linked together to form a ring;
$R_4$ is H or optionally substituted $C_1$-$C_3$ alkyl; and
$R_5$ is linked to $R_3$ by a group of formula COO(CR'R")O to form a ring, where R' and R" are independently H, optionally substituted $C_1$-$C_3$ alkyl, or are linked together to form a ring.

Exemplary compounds may be of formula

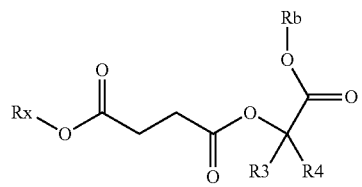

where $R_3$ is linked together with Rb to form a ring;
$R_4$ is H, optionally substituted $C_1$-$C_3$ alkyl;
$R_b$ is linked to $R_3$; and
$R_x$ is H or a pharmaceutically acceptable salt or alkyl or optionally substituted alkyl or a group of formula (II) where formula (II) is

where $R_3$ is H, optionally substituted $C_1$-$C_3$ alkyl, optionally substituted O—$C_1$-$C_3$ alkyl, or is linked together with $R_4$ or $R_5$ to form a ring;
$R_4$ is H, optionally substituted $C_1$-$C_3$ alkyl, or is linked together with $R_3$ to form a ring;
$R_5$ is selected from $OCOR_a$, $OCOOR_b$, $COOR_b$, $OCONR_cR_d$, $SO_2R_e$, $OPO(OR_f)(OR_g)$ or $CONR_cR_d$ or $R_5$ is linked to $R_3$ to form a ring containing one or more OCR'R"O linkages where R' and R" are independently H, optionally substituted $C_1$-$C_3$ alkyl, or are linked together to form a ring;
$R_a$ is optionally substituted alkyl or optionally substituted cycloalkyl;

$R_b$ is optionally substituted alkyl;
$R_c$ and $R_d$ are independently H, optionally substituted alkyl or are linked together to form a ring which may contain one or more further heteroatoms;
$R_e$ is optionally substituted alkyl; and
$R_f$ and $R_g$ are independently, H, methyl, ethyl or are linked together to form a ring.

In such cases $R_3$ and $R_5$ can be linked by a group to form a ring containing one or more OCR'R"O linkages where R' and R" are independently H, optionally substituted $C_1$-$C_3$ alkyl, or are linked together to form a ring. $R_3$ and $R_5$ can be linked by a group of formula COO(CR'R")O to form a ring.

Where $R_3$ and $R_b$ are linked together to form a ring, the ring can comprise a moiety of formula (V) where formula (V) is

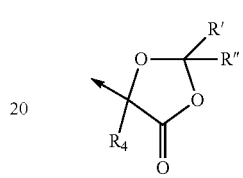

wherein $R_4$ is H or optionally substituted $C_1$-$C_3$ alkyl and R' and R" are independently H, optionally substituted $C_1$-$C_3$ alkyl, or are linked together to form a ring. R' and R" can each be methyl.

One or both ends of the succinate may contain the ring as shown above. Where both ends of the succinate contain the ring, the compound may be a compound according to formula (Va) where formula (Va) is

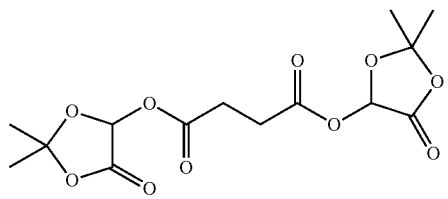 [SMILES: CC1(C)OC(=O)C(OC(=O)CCC(=O)OC2OC(C)(C)OC2=O)O1]

Exemplary compounds can be of type

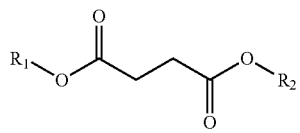

wherein $R_1$ is H or an optionally substituted alkyl group or a group of formula (II) and $R_2$ is independently a group according to formula (II) where formula (II) is

wherein $R_3$ and $R_4$ are independently H, optionally substituted $C_1$-$C_3$ alkyl, or are linked together to form a ring and $R_5$ is selected from $OCONR_cR_d$ or $CONR_cR_d$ where $R_c$ and $R_d$ are independently H, alkyl, optionally substituted alkyl or are linked together to form a ring which may contain one or more further heteroatoms. In such cases each Rc and Rd can be methyl or ethyl.

Exemplary compounds may be of formula

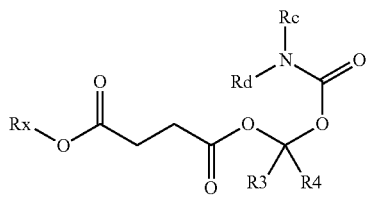

where $R_3$ and $R_4$ are independently H, optionally substituted $C_1$-$C_3$ alkyl, or are linked together to form a ring, $R_c$ and $R_d$ are independently H, alkyl, optionally substituted alkyl or are linked together to form a ring which may contain one or more further heteroatoms and $R_x$ is H or a pharmaceutically acceptable salt or alkyl or optionally substituted alkyl or a group of formula (II) where formula (II) is

where $R_3$ and $R_4$ are independently H, optionally substituted $C_1$-$C_3$ alkyl, or are linked together to form a ring and where $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring. In such cases each Rc and Rd can be methyl or ethyl.

Exemplary compounds may be of formula

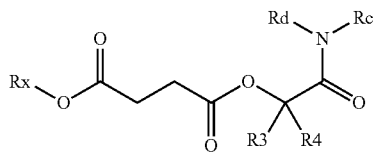

where $R_3$ and $R_4$ are independently H, optionally substituted $C_1$-$C_3$ alkyl, or are linked together to form a ring, $R_c$ and $R_d$ are independently H, alkyl, optionally substituted alkyl or are linked together to form a ring which may contain one or more further heteroatoms and $R_x$ is H or a pharmaceutically acceptable salt or alkyl or optionally substituted alkyl or a group of formula (II) where formula (II) is

where $R_3$ and $R_4$ are independently H, optionally substituted $C_1$-$C_3$ alkyl, or are linked together to form a ring and where $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring. In such cases each Rc and Rd can be methyl or ethyl.

Exemplary compounds can be of type

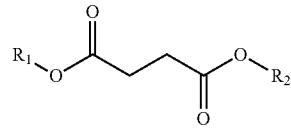

wherein $R_1$ is H or an optionally substituted alkyl group or a group of formula (II) and $R_2$ is independently a group according to formula (II) where formula (II) is

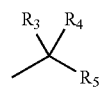

wherein $R_3$ and $R_4$ are independently H, optionally substituted $C_1$-$C_3$ alkyl, or are linked together to form a ring and $R_5$ is $SO_2R_e$ where $R_e$ is optionally substituted alkyl.

Exemplary compounds may be of formula

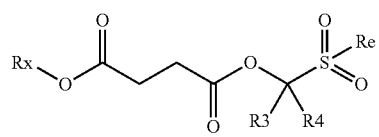

where $R_3$ and $R_4$ are independently H, optionally substituted $C_1$-$C_3$ alkyl, or are linked together to form a ring, $R_e$ is alkyl, cycloalkyl, optionally substituted alkyl or an amino or substituted amino group and $R_x$ is H or a pharmaceutically acceptable salt or alkyl or optionally substituted alkyl or a group of formula (II) where formula (II) is

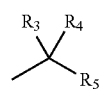

where $R_3$ and $R_4$ are independently H, optionally substituted $C_1$-$C_3$ alkyl, or are linked together to form a ring and where $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

Exemplary compounds can be of type

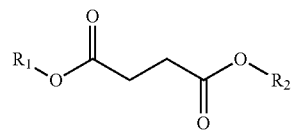

wherein $R_1$ is H or an optionally substituted alkyl group or a group of formula (II) and $R_2$ is independently a group according to formula (II) where formula (II) is

wherein $R_3$ and $R_4$ are independently H, optionally substituted $C_1$-$C_3$ alkyl, or are linked together to form a ring and $R_5$ is OPO(OR$_f$)(OR$_g$) where $R_f$ and $R_g$ are independently, H, methyl, ethyl or are linked together to form a ring.

Exemplary compounds may be of formula

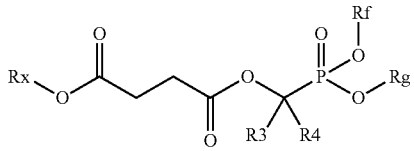

where $R_3$ and $R_4$ are independently H, optionally substituted $C_1$-$C_3$ alkyl, or are linked together to form a ring, $R_f$ and $R_g$ are independently, H, a pharmaceutically acceptable salt, methyl, ethyl, propyl or are linked together to form a ring and $R_x$ is H or a pharmaceutically acceptable salt or alkyl or optionally substituted alkyl or a group of formula (II) where formula (II) is

where $R_3$ and $R_4$ are independently H, optionally substituted $C_1$-$C_3$ alkyl, or are linked together to form a ring and where $R_5$ is selected from OCOR$_a$, OCOOR$_b$, OCONR$_c$R$_d$, SO$_2$R$_e$, OPO(OR$_f$)(OR$_g$) or CONR$_c$R$_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

Exemplary examples include compounds where one or both ends of the succinate compound is protected with a moiety selected from:

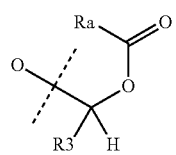

where $R_3$ is H, methyl or ethyl and Ra is CH$_3$, CH$_2$CH$_3$, CH(CH$_3$)$_2$ or C(CH$_3$)$_3$.

The other end of the succinate can be H or a pharmaceutically acceptable salt or optionally substituted alkyl group or a group of formula (II) where formula (II) is

where $R_3$ and $R_4$ are independently H, optionally substituted $C_1$-$C_3$ alkyl, or are linked together to form a ring and where $R_5$ is selected from OCOR$_a$, OCOOR$_b$, OCONR$_c$R$_d$, SO$_2$R$_e$, OPO(OR$_f$)(OR$_g$) or CONR$_c$R$_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

Exemplary examples include compounds where one of the ends of the succinate compound is protected with a moiety selected from:

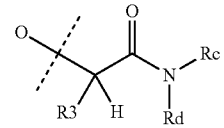

where $R_3$ is H, methyl or ethyl and $R_c$ and $R_d$ are independently H, CH$_3$, or CH$_2$CH$_3$.

The other end of the succinate can be H or a pharmaceutically acceptable salt or optionally substituted alkyl group or a group of formula (II) where formula (II) is

where $R_3$ and $R_4$ are independently H, optionally substituted $C_1$-$C_3$ alkyl, or are linked together to form a ring and where $R_5$ is selected from OCOR$_a$, OCOOR$_b$, OCONR$_c$R$_d$, SO$_2$R$_e$, OPO(OR$_f$)(OR$_g$) or CONR$_c$R$_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

Exemplary compounds can include those of formula

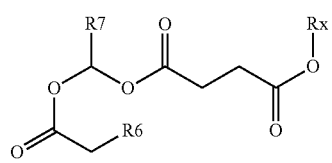

where $R_7$ is H, methyl or ethyl, R6 is H or methyl and $R_x$ is H or a pharmaceutically acceptable salt or alkyl or optionally substituted alkyl or a group of formula (II) where formula (II) is

where $R_3$ and $R_4$ are independently H, optionally substituted $C_1$-$C_3$ alkyl, or are linked together to form a ring and where $R_5$ is selected from $OCOR_a$, $OCOOR_b$, $OCONR_cR_d$, $SO_2R_e$, $OPO(OR_f)(OR_g)$ or $CONR_cR_d$ where $R_a$ is optionally substituted alkyl, $R_b$ is optionally substituted alkyl, $R_c$ and $R_d$ are independently H, optionally substituted alkyl or are linked together to form a ring which may contain one or more further heteroatoms, $R_e$ is optionally substituted alkyl, $R_f$ and $R_g$ are independently, H, methyl, ethyl or are linked together to form a ring.

Exemplary compounds can include those of formula

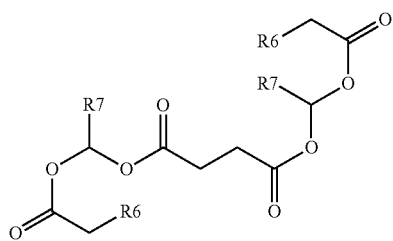

where each $R_7$ is independently H, methyl or ethyl and each $R_6$ is independently H or methyl.

Exemplary compounds can include dissuccinates where two succinate moieties are linked together via an acetal linkage. Exemplary compounds can include those of formula

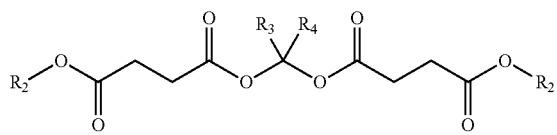

wherein $R_3$ and $R_4$ are independently H, optionally substituted $C_1$-$C_3$ alkyl, or are linked together to form a ring and each $R_2$ may be independently a group according to formula (II) where formula (II) is

wherein $R_3$ is H, optionally substituted $C_1$-$C_3$ alkyl, or is linked together with $R_5$ by a group of formula COO(CR'R")O to form a ring, where R' and R" are independently H, optionally substituted $C_1$-$C_3$ alkyl, or are linked together to form a ring;

$R_4$ is H;

$R_5$ is $OCOR_a$, $OCOOR_b$, $OCONR_cR_d$, $SO_2R_e$, $OPO(OR_f)(OR_g)$, $CONR_cR_d$ or is linked to $R_3$ by a group of formula COO(CR'R")O to form a ring, where R' and R" are independently H, optionally substituted $C_1$-$C_3$ alkyl, or are linked together to form a ring; where $R_a$ is optionally substituted $C_1$-$C_3$ alkyl or cycloalkyl;

$R_b$ is optionally substituted $C_1$-$C_3$ alkyl;

$R_c$ and $R_d$ are independently H, optionally substituted alkyl or are linked together to form a ring which may contain one or more further heteroatoms; $R_e$ is optionally substituted alkyl; and $R_f$ and $R_g$ are independently, H, methyl, ethyl or are linked together to form a ring.

Exemplary compounds can include those of formula XV

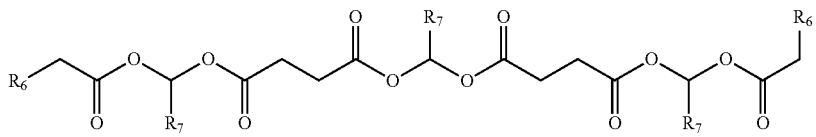

where each $R_7$ is independently H, methyl or ethyl and each $R_6$ is independently H or methyl The compound may be selected from

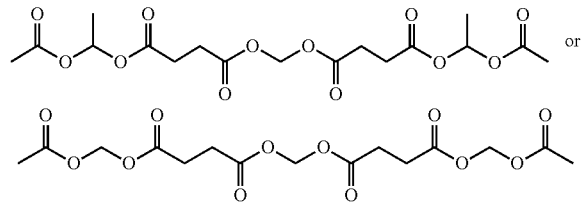

The compound may be a compound according to formula

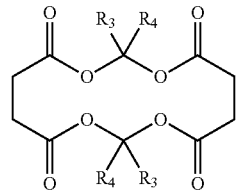

wherein $R_3$ and $R_4$ are independently H, optionally substituted $C_1$-$C_3$ alkyl, or are linked together to form a ring.

Exemplary compounds can include those of formula XIII

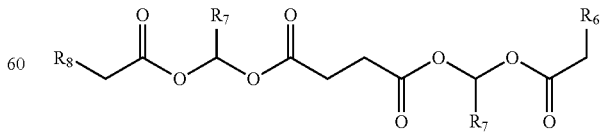

where each $R_7$ is independently H, methyl or ethyl, $R_6$ is independently H or methyl and $R_8$ is H, methyl or a moiety according to formula

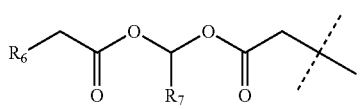

where $R_7$ is independently H, methyl or ethyl and $R_6$ is independently H or methyl.

Consequently, in a specific embodiment the exemplary compounds may be according to formula XIII

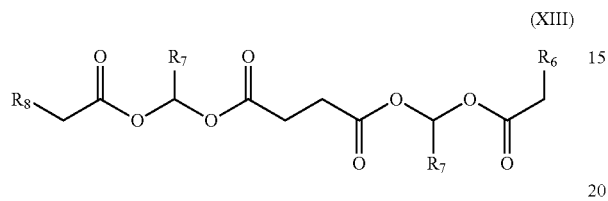

(XIII)

wherein each $R_6$ and $R_8$ is H and wherein each $R_7$ is independently H or methyl.

In a further specific embodiment, the exemplary compounds may be according to formula (XIII)

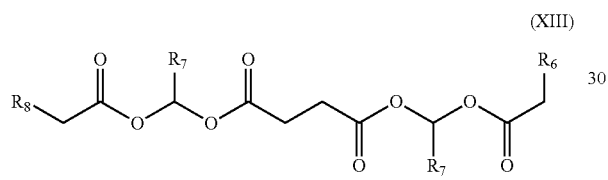

(XIII)

Wherein $R_6$ is H and wherein each $R_7$ is independently H or methyl, and wherein $R_8$ is a moiety according to formula

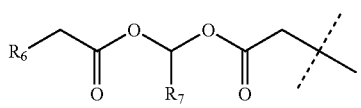

Exemplary compounds can include those of formula

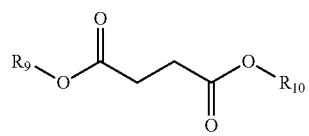

where $R_g$ is a moiety selected from;
i) a moiety of formula (V) where formula (V) is

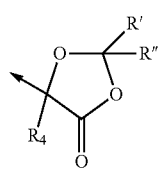

(V)

where $R_4$ is H or optionally substituted $C_1$-$C_3$ alkyl and R' and R" are independently H, optionally substituted $C_1$-$C_3$ alkyl, or are linked together to form a ring; or ii) a moiety of formula (II)

(II)

where $R_4$ is H, $R_3$ is H or optionally substituted $C_1$-$C_3$ alkyl and $R_5$ is $OCOR_a$, where $R_a$ is optionally substituted methyl, ethyl or cycloalkyl or forms part of a further succinate $CH_2CH_2CO_2$— moiety; and $R_{10}$ is a moiety selected from;
i) a moiety of formula (V) where formula (V) is

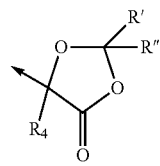

(V)

where $R_4$ is H or optionally substituted $C_1$-$C_3$ alkyl and R' and R" are independently H, optionally substituted $C_1$-$C_3$ alkyl, or are linked together to form a ring;

ii) a moiety of formula (II)

(II)

where $R_4$ is H, $R_3$ is H or optionally substituted $C_1$-$C_3$ alkyl and $R_5$ is $OCOR_a$, where $R_a$ is optionally substituted methyl, ethyl or cycloalkyl.

Compounds of the invention may include a succinate or di-succinate compound having one or more of the succinic acid carboxyl groups protected by the following groups:

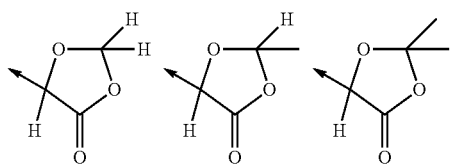

-continued

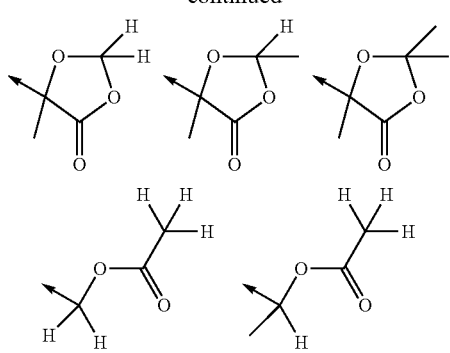

-continued

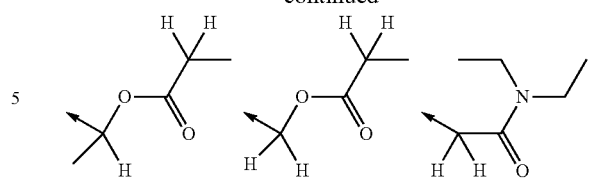

Known compounds succinic acid bis(2,2-dimethylpropionyloxymethyl)ester, succinic acid dibutyryloxymethyl ester and succinic acid bis-(1-butyryloxy-ethyl)ester can be disclaimed from any particular claim as required.

Exemplary compounds are shown below as examples 1-18:

| | | |
|---|---|---|
| 1 | 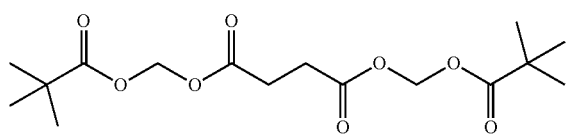 [SMILES: CC(C)(C)C(=O)OCOC(=O)CCC(=O)OCOC(=O)C(C)(C)C] | succinic acid bis (2,2-dimethylpropionyloxymethyl) ester; compound AN-192 in WO0228345 |
| 2 | 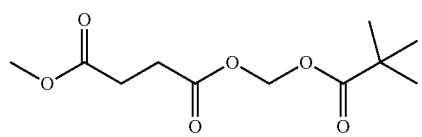 [SMILES: COC(=O)CCC(=O)OCOC(=O)C(C)(C)C] | Succinic acid 2,2-dimethyl-propionyloxymethyl ester methyl ester |
| 3 | 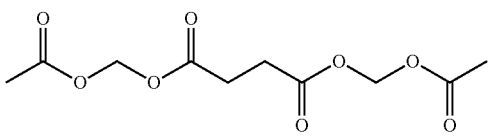 [SMILES: CC(=O)OCOC(=O)CCC(=O)OCOC(C)=O] | Succinic acid diacetoxymethyl ester |
| 4 | 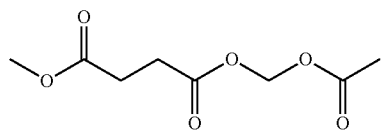 | Succinic acid acetoxymethyl ester methyl ester |
| 5 | 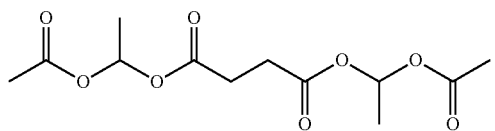 [SMILES: CC(=O)OC(C)OC(=O)CCC(=O)OC(C)OC(C)=O] | Succinic acid bis-(1-acetoxy-ethyl) ester |
| 6 | 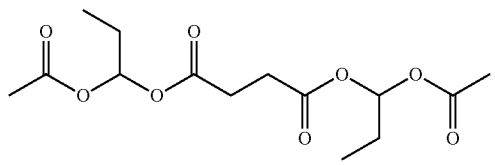 [SMILES: CCC(OC(C)=O)OC(=O)CCC(=O)OC(CC)OC(C)=O] | Succinic acid 1-acetoxy-ethyl ester methyl ester |
| 7 | 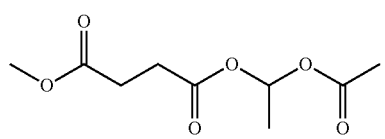 | Succinic acid bis-(1-acetoxy-propyl) ester |
| 8 | 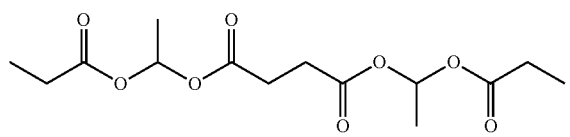 [SMILES: CCC(=O)OC(C)OC(=O)CCC(=O)OC(C)OC(=O)CC] | Succinic acid bis-(1-propionyloxy-ethyl) ester |

-continued

| | | |
|---|---|---|
| 9 | 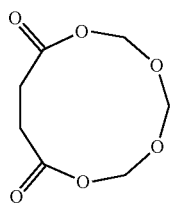 [SMILES: O=C1CCC(=O)OCOCOCO1] | 1,3,5,7-Tetraoxa-cycloundecane-8,11-dione |
| 10 | 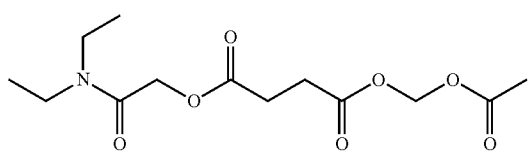 [SMILES: CCN(CC)C(=O)COC(=O)CCC(=O)OCOC(C)=O] | Succinic acid acetoxymethyl ester diethylcarbamoylmethyl ester |
| 11 | 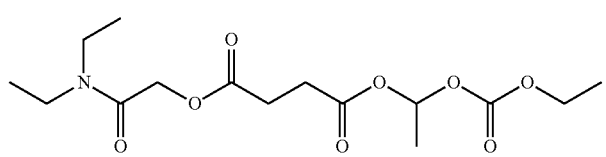 [SMILES: CCOC(=O)OC(C)OC(=O)CCC(=O)OCC(=O)N(CC)CC] | Succinic acid diethylcarbamoylmethyl ester 1-ethoxycarbonyloxy-ethyl ester |
| 12 | 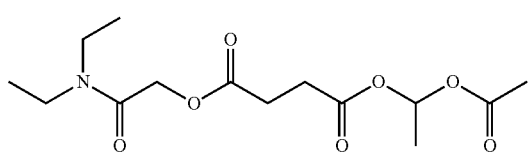 [SMILES: CCN(CC)C(=O)COC(=O)CCC(=O)OC(C)OC(C)=O] | Succinic acid 1-acetoxy-ethyl ester diethylcarbamoylmethyl ester |
| 13 | 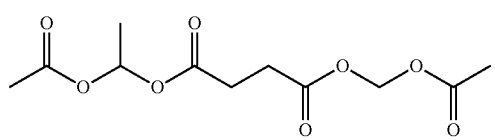 [SMILES: CC(=O)OCOC(=O)CCC(=O)OC(C)OC(C)=O] | Succinic acid 1-acetoxy-ethyl ester acetoxymethyl ester |
| 14 | 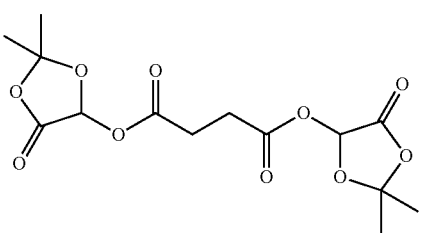 | Succinic acid bis-(2,2-dimethyl-5-oxo-[1,3]dioxolan-4-yl) ester |
| 15 | 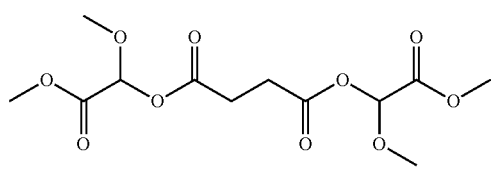 | Succinic acid bis-(methoxy-methoxycarbonyl-methyl) ester |
| 16 | 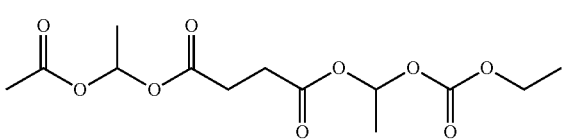 [SMILES: CCOC(=O)OC(C)OC(=O)CCC(=O)OC(C)OC(C)=O] | Succinic acid 1-acetoxy-ethyl ester 1-ethoxycarbonyloxy-ethyl ester |
| 17 | 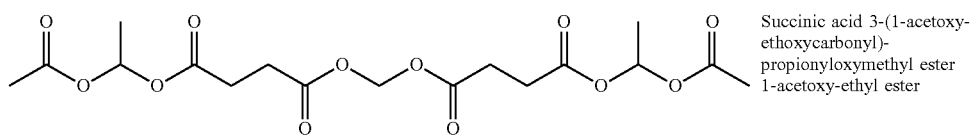 | Succinic acid 3-(1-acetoxy-ethoxycarbonyl)-propionyloxymethyl ester 1-acetoxy-ethyl ester |

| 18 | 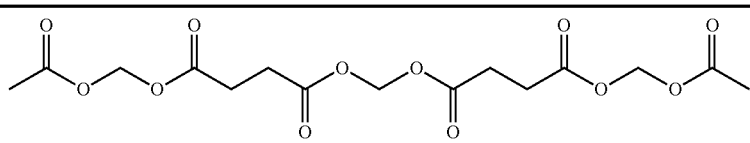 | Succinic acid 3-acetoxymethoxycarbonyl-propionyloxymethyl ester acetoxymethyl ester |

Methods for Preparing the Protected Succinates of the Invention

The skilled person will recognise that the protected succinates of the invention may be prepared, in known manner, in a variety of ways. The routes below are merely illustrative of some methods that can be employed for the synthesis of compounds of formula (I).

The present invention further provides a process for the preparation of a compound of formula (I) which comprises reacting succinic acid with compound of formula (VI)

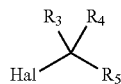

wherein Hal represents a halogen (e.g. F, Cl, Br or I) and $R_3$, $R_4$ and $R_5$ are as defined in formula (I).

The reaction of succinic acid and the compound for formula (VI) may conveniently be carried out in a solvent such as dichloromethane, acetone, acetonitrile or N,N-dimethylformamide with a suitable base such as triethylamine, diisopropylethylamine or caesium carbonate at a temperature, for example, in the range from −10° C. to 80° C., particularly at room temperature. The reaction may be performed with optional additives such as sodium iodide or tetraalkyl ammonium halides (e.g. tetrabutyl ammonium iodide).

For compounds of formula (I) wherein $R_1$ and $R_2$ are different groups of formula (II), the compound of formula (I) may be prepared by reacting a group of formula (VII)

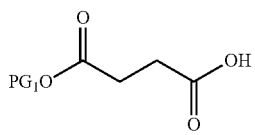

(VII)

wherein $PG_1$ is a protecting group such as tert-butyl, benzyl or 4-methoxybenzyl, with a group of formula (VI) under the conditions outlined above followed by deprotection of the protecting group under appropriate conditions such as trifluoroacetic acid or hydrochloric acid in a solvent such as dichloromethane or by hydrogenation (aryl groups) with a catalyst such as palladium on carbon in a solvent such as ethyl acetate, followed by reaction of the resulting compound with a different group of formula (VI) under the conditions outlined above to react with the deprotected carboxylate.

For compounds of formula (I) wherein $R_1$ is an optionally substituted alkyl group and $R_2$ is a group of formula (II), the compound of formula (I) may be prepared by reacting a group of formula (VIII)

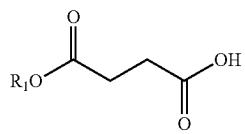

with a group of formula (VI) under the conditions outlined above.

Protected di-succinate compounds may conveniently be prepared by reaction of a group of formula (IX)

(IX)

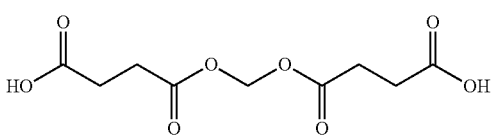

with a group of formula (VI) under the conditions outlined above. Compounds of formula (IX) may be conveniently prepared by reaction of a compound of formula (VII) with dichloromethane in a suitable solvent such as dichloromethane with a suitable additive such as tetrabutylhydrogensulfate. The resulting bis-ester may be subsequently hydrolysed by treatment with an acid such as trifluoroacetic acid or hydrochloric acid in a solvent such as dichloromethane to afford compounds of formula (IX).

Compounds of formula (VII) and (VIII) are either commercially available or may be conveniently prepared by literature methods such as those outlined in Journal of Organic Chemistry, 72(19), 7253-7259; 2007.

Compounds of formula (VI)

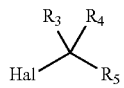

are either commercially available or may be conveniently prepared by literature methods such as those outlined in Journal of the American Chemical Society, 43, 660-7; 1921 or Journal of medicinal chemistry (1992), 35(4), 687-94.

Salts and Isomers of the Protected Succinates of the Invention

The disclosures herein include any pharmaceutically acceptable salts. Where compounds are isomers, all chiral forms and racemates are included. The disclosures include all solvates, hydrates and crystal forms.

To the extent that any of the compounds described have chiral centres, the present invention extends to all optical isomers of such compounds, whether in the form of racemates or resolved enantiomers. The invention described herein relates to all crystal forms, solvates and hydrates of any of the disclosed compounds however so prepared. To the extent that any of the compounds disclosed herein have acid or basic centres such as carboxylates or amino groups, then all salt forms of said compounds are included herein. In the case of pharmaceutical uses, the salt should be seen as being a pharmaceutically acceptable salt.

Pharmaceutically acceptable salts that may be mentioned include acid addition salts and base addition salts. Such salts may be formed by conventional means, for example by reaction of a free acid or a free base form of a compound with one or more equivalents of an appropriate acid or base, optionally in a solvent, or in a medium in which the salt is insoluble, followed by removal of said solvent, or said medium, using standard techniques (e.g. in vacuo, by freeze-drying or by filtration). Salts may also be prepared by exchanging a counter-ion of a compound in the form of a salt with another counter-ion, for example using a suitable ion exchange resin.

Examples of pharmaceutically acceptable salts include acid addition salts derived from mineral acids and organic acids, and salts derived from metals such as sodium, magnesium, or preferably, potassium and calcium or organic bases such as ammonium, ethanolamine, N,N-dialkylethanolamines or morpholine salts.

Examples of acid addition salts include acid addition salts formed with acetic, 2,2-dichloroacetic, adipic, alginic, aryl sulfonic acids (e.g. benzenesulfonic, naphthalene-2-sulfonic, naphthalene-1,5-disulfonic and p-toluenesulfonic), ascorbic (e.g. L-ascorbic), L-aspartic, benzoic, 4-acetamidobenzoic, butanoic, (+) camphoric, camphor-sulfonic, (+)-(1S)-camphor-10-sulfonic, capric, caproic, caprylic, cinnamic, citric, cyclamic, dodecylsulfuric, ethane-1,2-disulfonic, ethanesulfonic, 2-hydroxyethanesulfonic, formic, fumaric, galactaric, gentisic, glucoheptonic, gluconic (e.g. D-gluconic), glucuronic (e.g. D-glucuronic), glutamic (e.g. L-glutamic), α-oxoglutaric, glycolic, hippuric, hydrobromic, hydrochloric, hydriodic, isethionic, lactic (e.g. (+)-L-lactic and (±)-DL-lactic), lactobionic, maleic, malic (e.g. (−)-L-malic), malonic, (±)-DL-mandelic, metaphosphoric, methanesulfonic, 1-hydroxy-2-naphthoic, nicotinic, nitric, oleic, orotic, oxalic, palmitic, pamoic, phosphoric, propionic, L-pyroglutamic, salicylic, 4-amino-salicylic, sebacic, stearic, succinic, sulfuric, tannic, tartaric (e.g. (+)-L-tartaric), thiocyanic, undecylenic and valeric acids.

Particular examples of salts are salts derived from mineral acids such as hydrochloric, hydrobromic, phosphoric, metaphosphoric, nitric and sulfuric acids; from organic acids, such as tartaric, acetic, citric, malic, lactic, fumaric, benzoic, glycolic, gluconic, succinic, arylsulfonic acids; and from metals such as sodium, magnesium, or preferably, potassium and calcium.

Also encompassed are any solvates of the compounds and their salts. Preferred solvates are solvates formed by the incorporation into the solid state structure (e.g. crystal structure) of the compounds of the invention of molecules of a non-toxic pharmaceutically acceptable solvent (referred to below as the solvating solvent). Examples of such solvents include water, alcohols (such as ethanol, isopropanol and butanol) and dimethylsulfoxide. Solvates can be prepared by recrystallising the compounds of the invention with a solvent or mixture of solvents containing the solvating solvent. Whether or not a solvate has been formed in any given instance can be determined by subjecting crystals of the compound to analysis using well known and standard techniques such as thermogravimetric analysis (TGE), differential scanning calorimetry (DSC) and X-ray crystallography.

The solvates can be stoichiometric or non-stoichiometric solvates. Particular solvates may be hydrates, and examples of hydrates include hemihydrates, monohydrates and dihydrates.

For a more detailed discussion of solvates and the methods used to make and characterise them, see Bryn et al., Solid-State Chemistry of Drugs, Second Edition, published by SSCI, Inc of West Lafayette, Ind., USA, 1999, ISBN 0-967-06710-3.

Mitochondria

Mitochondria are organelles in eukaryotic cells, popularly referred to as the "powerhouse" of the cell. One of their primary functions is oxidative phosphorylation. The molecule adenosine triphosphate (ATP) functions as an energy "currency" or energy carrier in the cell, and eukaryotic cells derive the majority of their ATP from biochemical processes carried out by mitochondria. These biochemical processes include the citric acid cycle (the tricarboxylic acid cycle, or Kreb's cycle), which generates reduced nicotinamide adenine dinucleotide ($NADH^+H^{<+>}$) from oxidized nicotinamide adenine dinucleotide ($NAD^{<+>}$) and reduced flavin adenine dinucleotide ($FADH_2$) from oxidized flavin adenine dinucleotide (FAD), as well as oxidative phosphorylation, during which $NADH^+H^{<+>}$ and $FADH_2$ is oxidized back to $NAD^{<+>}$ and FAD.

The electrons released by oxidation of $NADH^+H^{<+>}$ are shuttled down a series of protein complexes (Complex I, Complex II, Complex III, and Complex IV) known as the respiratory chain. The oxidation of succinate occurs at Complex II (succinate dehydrogenase complex) and FAD is part of the complex. The respiratory complexes are embedded in the inner membrane of the mitochondrion. Complex IV, at the end of the chain, transfers the electrons to oxygen, which is reduced to water. The energy released as these electrons traverse the complexes is used to generate a proton gradient across the inner membrane of the mitochondrion, which creates an electrochemical potential across the inner membrane. Another protein complex, Complex V (which is not directly associated with Complexes I, II, III and IV) uses the energy stored by the electrochemical gradient to convert ADP into ATP.

The citric acid cycle and oxidative phosphorylation are preceded by glycolysis, in which a molecule of glucose is broken down into two molecules of pyruvate, with net generation of two molecules of ATP per molecule of glucose. The pyruvate molecules then enter the mitochondria, where they are completely oxidized to $CO_2$ and $H_2O$ via oxidative phosphorylation (the overall process is known as aerobic respiration). The complete oxidation of the two pyruvate molecules to carbon dioxide and water yields about at least 28-29 molecules of ATP, in addition to the 2 molecules of ATP generated by transforming glucose into two pyruvate molecules. If oxygen is not available, the pyruvate molecule does not enter the mitochondria, but rather is converted to lactate, in the process of anaerobic respiration.

The overall net yield per molecule of glucose is thus approximately at least 30-31 ATP molecules. ATP is used to power, directly or indirectly, almost every other biochemical reaction in the cell. Thus, the extra (approximately) at least 28 or 29 molecules of ATP contributed by oxidative phosphorylation during aerobic respiration are critical to the proper functioning of the cell. Lack of oxygen prevents aerobic respiration and will result in eventual death of almost all aerobic organisms; a few organisms, such as yeast, are able to survive using either aerobic or anaerobic respiration.

When cells in an organism are temporarily deprived of oxygen, anaerobic respiration is utilized until oxygen again becomes available or the cell dies. The pyruvate generated during glycolysis is converted to lactate during anaerobic respiration. The build-up of lactic acid is believed to be responsible for muscle fatigue during intense periods of activity, when oxygen cannot be supplied to the muscle cells. When oxygen again becomes available, the lactate is converted back into pyruvate for use in oxidative phosphorylation.

Mitochondrial dysfunction contributes to various disease states. Some mitochondrial diseases are due to mutations or deletions in the mitochondrial genome. If a threshold proportion of mitochondria in the cell is defective, and if a threshold proportion of such cells within a tissue have defective mitochondria, symptoms of tissue or organ dysfunction can result. Practically any tissue can be affected, and a large variety of symptoms may be present, depending on the extent to which different tissues are involved.

Use of the Compounds of the Invention

The compounds of the invention may be used in any situation where an enhanced energy production (ATP) is desired. Examples are e.g. in all clinical conditions where there is a potential benefit of increased mitochondrial ATP-production or a restoration of mitochondrial function, such as in the treatment of cancer and following hypoxia, ischemia, stroke, myocardial infarction, acute angina, an acute kidney injury, coronary occlusion and atrial fibrillation The compounds may also be useful in the prevention or limitations of reperfusion injuries.

In particular, the compounds of the invention can be used in medicine, notably in the treatment or prevention of a mitochondria-related disease or disorder or in cosmetics.

Dysfunction of mitochondria is also described in relation to renal tubular acidosis; motor neuron diseases; other neurological diseases; epilepsy; genetic diseases; Huntington's Disease; mood disorders; schizophrenia; bipolar disorder; age-associated diseases; cerebral vascular accidents, macular degeneration; diabetes; and cancer.

Compounds of the Invention for Use in Mitochondrial Related Disorders or Diseases The compounds according to the invention may be used in the prevention or treatment a mitochondria-related disease selected from the following:
  Alpers Disease (Progressive Infantile Poliodystrophy)
  Amyotrophic lateral sclerosis (ALS)
  Autism
  Barth syndrome (Lethal Infantile Cardiomyopathy)
  Beta-oxidation Defects
  Bioenergetic metabolism deficiency
  Carnitine-Acyl-Carnitine Deficiency
  Carnitine Deficiency
  Creatine Deficiency Syndromes (Cerebral Creatine Deficiency Syndromes (CCDS) includes: Guanidinoaceteate Methyltransferase Deficiency (GAMT Deficiency), L-Arginine: Glycine Amidinotransferase Deficiency (AGAT Deficiency), and SLC6A8-Related Creatine Transporter Deficiency (SLC6A8 Deficiency).
  Co-Enzyme Q10 Deficiency
  Complex I Deficiency (NADH dehydrogenase (NADH-CoQ reductase) deficiency)
  Complex II Deficiency (Succinate dehydrogenase deficiency)
  Complex III Deficiency (Ubiquinone-cytochrome c oxidoreductase deficiency)
  Complex IV Deficiency/COX Deficiency (Cytochrome c oxidase deficiency is caused by a defect in Complex IV of the respiratory chain)
  Complex V Deficiency (ATP synthase deficiency)
  COX Deficiency
  CPEO (Chronic Progressive External Ophthalmoplegia Syndrome)
  CPT I Deficiency
  CPT II Deficiency
  Friedreich's ataxia (FRDA or FA)
  Glutaric Aciduria Type II
  KSS (Kearns-Sayre Syndrome)
  Lactic Acidosis
  LCAD (Long-Chain Acyl-CoA Dehydrogenase Deficiency)
  LCHAD
  Leigh Disease or Syndrome (Subacute Necrotizing Encephalomyelopathy)
  LHON (Leber's hereditary optic neuropathy)
  Luft Disease
  MCAD (Medium-Chain Acyl-CoA Dehydrogenase Deficiency)
  MELAS (Mitochondrial Encephalomyopathy Lactic Acidosis and Strokelike Episodes)
  MERRF (Myoclonic Epilepsy and Ragged-Red Fiber Disease)
  MIRAS (Mitochondrial Recessive Ataxia Syndrome)
  Mitochondrial Cytopathy
  Mitochondrial DNA Depletion
  Mitochondrial Encephalopathy includes: Encephalomyopathy, Encephalomyelopathy
  Mitochondrial Myopathy
  MNGIE (Myoneurogastointestinal Disorder and Encephalopathy)
  NARP (Neuropathy, Ataxia, and Retinitis Pigmentosa)
  Neurodegenerative disorders associated with Parkinson's, Alzheimer's or Huntington's disease
  Pearson Syndrome
  Pyruvate Carboxylase Deficiency
  Pyruvate Dehydrogenase Deficiency
  POLG Mutations
  Respiratory Chain Deficiencies
  SCAD (Short-Chain Acyl-CoA Dehydrogenase Deficiency)
  SCHAD
  VLCAD (Very Long-Chain Acyl-CoA Dehydrogenase Deficiency)

With reference to information from the web-page of United Mitochondrial Disease Foundation, some of the above-mentioned diseases are discussed in more details in the following:

Complex 1 Deficiency:

Inside the mitochondrion is a group of proteins that carry electrons along four chain reactions (Complexes I-IV), resulting in energy production. This chain is known as the Electron Transport Chain. A fifth group (Complex V) churns out the ATP. Together, the electron transport chain and the ATP synthase form the respiratory chain and the whole process is known as oxidative phosphorylation or OXPHOS.

Complex I, the first step in this chain, is the most common site for mitochondrial abnormalities, representing as much as one third of the respiratory chain deficiencies. Often presenting at birth or in early childhood, Complex I deficiency is usually a progressive neurodegenerative disorder and is responsible for a variety of clinical symptoms, particularly in organs and tissues that require high energy levels, such as brain, heart, liver, and skeletal muscles. A number of specific mitochondrial disorders have been associated with Complex I deficiency including: Leber's hereditary optic neuropathy (LHON), MELAS, MERRF, and Leigh Syndrome (LS).

LHON is characterized by blindness which occurs on average between 27 and 34 years of age; blindness can develop in both eyes simultaneously, or sequentially (one eye will develop blindness, followed by the other eye two months later on average). Other symptoms may also occur, such as cardiac abnormalities and neurological complications.

There are three major forms of Complex I deficiency:
i) Fatal infantile multisystem disorder—characterized by poor muscle tone, developmental delay, heart disease, lactic acidosis, and respiratory failure.
ii) Myopathy (muscle disease)—starting in childhood or adulthood, and characterized by weakness or exercise intolerance.
iii) Mitochondrial encephalomyopathy (brain and muscle disease)—beginning in childhood or adulthood and involving variable symptom combinations which may include: eye muscle paralysis, pigmentary retinopathy (retinal color changes with loss of vision), hearing loss, sensory neuropathy (nerve damage involving the sense organs), seizures, dementia, ataxia (abnormal muscle coordination), and involuntary movements. This form of Complex I deficiency may cause Leigh Syndrome and MELAS.

Most cases of Complex I deficiency result from autosomal recessive inheritance (combination of defective nuclear genes from both the mother and the father). Less frequently, the disorder is maternally inherited or sporadic and the genetic defect is in the mitochondrial DNA.

Treatment:

As with all mitochondrial diseases, there is presently no cure for Complex I deficiency. A variety of treatments, which may or may not be effective, can include such metabolic therapies as: riboflavin, thiamine, biotin, coenzyme Q10, carnitine, and ketogenic diet. Therapies for the infantile multisystem form have been unsuccessful.

The clinical course and prognosis for Complex I patients is highly variable and may depend on the specific genetic defect, age of onset, organs involved, and other factors.

Complex III Deficiency:

The symptoms include four major forms:
i) Fatal infantile encephalomyopathy, congenital lactic acidosis, hypotonia, dystrophic posturing, seizures, and coma. Ragged-red fibers in muscle tissue are common.
ii) Encephalomyopathies of later onset (childhood to adult life): various combinations of weakness, short stature, ataxia, dementia, hearing loss, sensory neuropathy, pigmentary retinopathy, and pyramidal signs. Ragged-red fibers are common. Possible lactic acidosis.
iii) Myopathy, with exercise intolerance evolving into fixed weakness. Ragged-red fibers are common. Possible lactic acidosis.
iv) Infantile histiocytoid cardiomyopathy.

Complex IV Deficiency/COX Deficiency:

The symptoms include two major forms:
1. Encephalomyopathy: Typically normal for the first 6 to 12 months of life and then show developmental regression, ataxia, lactic acidosis, optic atrophy, ophthalmoplegia, nystagmus, dystonia, pyramidal signs, and respiratory problems. Frequent seizures. May cause Leigh Syndrome
2. Myopathy: Two main variants:
   1. Fatal infantile myopathy: may begin soon after birth and accompanied by hypotonia, weakness, lactic acidosis, ragged-red fibers, respiratory failure, and kidney problems.
   2. Benign infantile myopathy: may begin soon after birth and accompanied by hypotonia, weakness, lactic acidosis, ragged-red fibers, respiratory problems, but (if the child survives) followed by spontaneous improvement.

KSS (Kearns-Sayre Syndrome):

KSS is a slowly progressive multi-system mitochondrial disease that often begins with drooping of the eyelids (ptosis). Other eye muscles eventually become involved, resulting in paralysis of eye movement. Degeneration of the retina usually causes difficulty seeing in dimly lit environments.

KSS is characterized by three main features:
typical onset before age 20 although may occur in infancy or adulthood
paralysis of specific eye muscles (called chronic progressive external ophthalmoplegia—CPEO)
degeneration of the retina causing abnormal accumulation of pigmented (colored) material (pigmentary retinopathy).

In addition, one or more of the following conditions is present:
block of electrical signals in the heart (cardiac conduction defects)
elevated cerebrospinal fluid protein
incoordination of movements (ataxia).

Patients with KSS may also have such problems as deafness, dementia, kidney dysfunction, and muscle weakness. Endocrine abnormalities including growth retardation, short stature, or diabetes may also be evident.

KSS is a rare disorder. It is usually caused by a single large deletion (loss) of genetic material within the DNA of the mitochondria (mtDNA), rather than in the DNA of the cell nucleus. These deletions, of which there are over 150 species, typically arise spontaneously. Less frequently, the mutation is transmitted by the mother.

As with all mitochondrial diseases, there is no cure for KSS.

Treatments are based on the types of symptoms and organs involved, and may include: Coenzyme Q10, insulin for diabetes, cardiac drugs, and a cardiac pacemaker which may be life-saving. Surgical intervention for drooping eyelids may be considered but should be undertaken by specialists in ophthalmic surgical centers.

KSS is slowly progressive and the prognosis varies depending on severity. Death is common in the third or fourth decade and may be due to organ system failures.

Leigh Disease or Syndrome (Subacute Necrotizing Encephalomyelopathy):

Symptoms: Seizures, hypotonia, fatigue, nystagmus, poor reflexes, eating and swallowing difficulties, breathing problems, poor motor function, ataxia.

Causes: Pyruvate Dehydrogenase Deficiency, Complex I Deficiency, Complex II Deficiency, Complex IV/COX Deficiency, NARP.

Leigh's Disease is a progressive neurometabolic disorder with a general onset in infancy or childhood, often after a viral infection, but can also occur in teens and adults. It is characterized on MRI by visible necrotizing (dead or dying tissue) lesions on the brain, particularly in the midbrain and brainstem.

The child often appears normal at birth but typically begins displaying symptoms within a few months to two years of age, although the timing may be much earlier or later. Initial symptoms can include the loss of basic skills such as sucking, head control, walking and talking. These may be accompanied by other problems such as irritability, loss of appetite, vomiting and seizures. There may be periods of sharp decline or temporary restoration of some functions. Eventually, the child may also have heart, kidney, vision, and breathing complications.

There is more than one defect that causes Leigh's Disease. These include a pyruvate dehydrogenase (PDHC) deficiency, and respiratory chain enzyme defects—Complexes I, II, IV, and V. Depending on the defect, the mode of inheritance may be X-linked dominant (defect on the X chromosome and disease usually occurs in males only), autosomal recessive (inherited from genes from both mother and father), and maternal (from mother only). There may also be spontaneous cases which are not inherited at all.

There is no cure for Leigh's Disease. Treatments generally involve variations of vitamin and supplement therapies, often in a "cocktail" combination, and are only partially effective. Various resource sites include the possible usage of: thiamine, coenzyme Q10, riboflavin, biotin, creatine, succinate, and idebenone. Experimental drugs, such as dichloroacetate (DCA) are also being tried in some clinics. In some cases, a special diet may be ordered and must be monitored by a dietitian knowledgeable in metabolic disorders.

The prognosis for Leigh's Disease is poor. Depending on the defect, individuals typically live anywhere from a few years to the mid-teens. Those diagnosed with Leigh-like syndrome or who did not display symptoms until adulthood tend to live longer.

MELAS (Mitochondrial Encephalomyopathy Lactic Acidosis and Stroke-like Episodes):

Symptoms: Short statue, seizures, stroke-like episodes with focused neurological deficits, recurrent headaches, cognitive regression, disease progression, ragged-red fibers.

Cause: Mitochondrial DNA point mutations: A3243G (most common)

MELAS—Mitochondrial Myopathy (muscle weakness), Encephalopathy (brain and central nervous system disease), Lactic Acidosis (build-up of a product from anaerobic respiration), and Stroke-like episodes (partial paralysis, partial vision loss, or other neurological abnormalities).

MELAS is a progressive neurodegenerative disorder with typical onset between the ages of 2 and 15, although it may occur in infancy or as late as adulthood. Initial symptoms may include stroke-like episodes, seizures, migraine headaches, and recurrent vomiting.

Usually, the patient appears normal during infancy, although short stature is common. Less common are early infancy symptoms that may include developmental delay, learning disabilities or attention-deficit disorder. Exercise intolerance, limb weakness, hearing loss, and diabetes may also precede the occurrence of the stroke-like episodes.

Stroke-like episodes, often accompanied by seizures, are the hallmark symptom of MELAS and cause partial paralysis, loss of vision, and focal neurological defects. The gradual cumulative effects of these episodes often result in variable combinations of loss of motor skills (speech, movement, and eating), impaired sensation (vision loss and loss of body sensations), and mental impairment (dementia). MELAS patients may also suffer additional symptoms including: muscle weakness, peripheral nerve dysfunction, diabetes, hearing loss, cardiac and kidney problems, and digestive abnormalities. Lactic acid usually accumulates at high levels in the blood, cerebrospinal fluid, or both.

MELAS is maternally inherited due to a defect in the DNA within mitochondria. There are at least 17 different mutations that can cause MELAS. By far the most prevalent is the A3243G mutation, which is responsible for about 80% of the cases.

There is no cure or specific treatment for MELAS. Although clinical trials have not proven their efficacy, general treatments may include such metabolic therapies as: CoQ10, creatine, phylloquinone, and other vitamins and supplements. Drugs such as seizure medications and insulin may be required for additional symptom management. Some patients with muscle dysfunction may benefit from moderate supervised exercise. In select cases, other therapies that may be prescribed include dichloroacetate (DCA) and menadione, though these are not routinely used due to their potential for having harmful side effects.

The prognosis for MELAS is poor. Typically, the age of death is between 10 to 35 years, although some patients may live longer. Death may come as a result of general body wasting due to progressive dementia and muscle weakness, or complications from other affected organs such as heart or kidneys.

MERRF is a progressive multi-system syndrome usually beginning in childhood, but onset may occur in adulthood. The rate of progression varies widely. Onset and extent of symptoms can differ among affected siblings.

The classic features of MERRF include:
Myoclonus (brief, sudden, twitching muscle spasms)—the most characteristic symptom
Epileptic seizures
Ataxia (impaired coordination)
Ragged-red fibers (a characteristic microscopic abnormality observed in muscle biopsy of patients with MERRF and other mitochondrial disorders) Additional symptoms may include: hearing loss, lactic acidosis (elevated lactic acid level in the blood), short stature, exercise intolerance, dementia, cardiac defects, eye abnormalities, and speech impairment.

Although a few cases of MERRF are sporadic, most cases are maternally inherited due to a mutation within the mitochondria. The most common MERRF mutation is A8344G, which accounted for over 80% of the cases. Four other mitochondrial DNA mutations have been reported to cause MERRF. While a mother will transmit her MERRF mutation to all of her offspring, some may never display symptoms.

As with all mitochondrial disorders, there is no cure for MERRF. Therapies may include coenzyme Q10, L-carnitine, and various vitamins, often in a "cocktail" combination. Management of seizures usually requires anticonvulsant drugs. Medications for control of other symptoms may also be necessary.

The prognosis for MERRF varies widely depending on age of onset, type and severity of symptoms, organs involved, and other factors.

Mitochondrial DNA Depletion:

The symptoms include three major forms:
1. Congenital myopathy: Neonatal weakness, hypotonia requiring assisted ventilation, possible renal dysfunction. Severe lactic acidosis. Prominent ragged-red fibers. Death due to respiratory failure usually occurs prior to one year of age.
2. Infantile myopathy: Following normal early development until one year old, weakness appears and worsens rapidly, causing respiratory failure and death typically within a few years.

3. Hepatopathy: Enlarged liver and intractable liver failure, myopathy. Severe lactic acidosis. Death is typical within the first year.

Friedreich's Ataxia

Friedreich's ataxia (FRDA or FA) an autosomal recessive neurodegenerative and cardiodegenerative disorder caused by decreased levels of the protein frataxin. Frataxin is important for the assembly of iron-sulfur clusters in mitochondrial respiratory-chain complexes. Estimates of the prevalence of FRDA in the United States range from 1 in every 22,000-29,000 people (see www.nlm.nih.gov/medlineplus/ency/article/001411.htm) to 1 in 50,000 people (see www.umc-cares.org/health_info/ADAM/Articles/001411.asp). The disease causes the progressive loss of voluntary motor coordination (ataxia) and cardiac complications. Symptoms typically begin in childhood, and the disease progressively worsens as the patient grows older; patients eventually become wheelchair-bound due to motor disabilities.

In addition to congenital disorders involving inherited defective mitochondria, acquired mitochondrial dysfunction has been suggested to contribute to diseases, particularly neurodegenerative disorders associated with aging like Parkinson's, Alzheimer's, and Huntington's Diseases. The incidence of somatic mutations in mitochondrial DNA rises exponentially with age; diminished respiratory chain activity is found universally in aging people. Mitochondrial dysfunction is also implicated in excitotoxicity, neuronal injury, cerebral vascular accidents such as that associated with seizures, stroke and ischemia.

Compositions Containing a Novel Compound of the Invention

The compounds of the invention may be contained in a composition suitable for use in medicine or in cosmetics. In the following the term composition is used to include compositions suitable for use in medicine or in cosmetics.

The term "composition" in the context of this invention means a composition comprising a compound of the invention and comprising additionally one or more pharmaceutically or cosmetically acceptable carriers. The composition may further contain ingredients selected from, for example, diluents, adjuvants, excipients, vehicles, preserving agents, fillers, disintegrating agents, wetting agents, emulsifying agents, suspending agents, sweetening agents, flavouring agents, perfuming agents, antibacterial agents, antifungal agents, lubricating agents and dispersing agents, depending on the nature of the mode of administration and dosage forms. The compositions may be designed to administration by the oral, parenteral or mucosal route and the choice or the specific form of composition is dependent on the administration route. Thus for oral administration the composition may be in the form, for example, of tablets, lozenges, dragees, films, powders, elixirs, syrups, liquid preparations including dispersions, suspensions, emulsions, solutions or sprays, cachets, granules, capsules, etc., For administration to mucosa the composition may be in the form of sprays, inhalants, dispersions, suspensions, emulsions, solutions, gels, patches, films, ointments, creams, lotions, suppositories etc. For parenteral administration the composition is in the form of a liquid preparation such as a solution, dispersion, emulsion or suspension including liposome compositions.

The dosages may be varied depending upon the requirements of the patient, the severity of the condition being treated, and the compound being employed. Determination of the proper dosage for a particular situation is within the skill of the art. Generally, treatment is initiated with the smaller dosages which are less than the optimum dose of the compound. Thereafter the dosage is increased by small increments until the optimum effect under the circumstances is reached. For convenience, the total daily dosage may be divided and administered in portions during the day if desired.

The magnitude of an effective dose of a compound will, of course, vary with the nature of the severity of the condition to be treated and with the particular compound and its route of administration. The selection of appropriate dosages is within the ability of one of ordinary skill in this art, without undue burden. In general, the daily dose range may be from about 1 mg to about 20 g per kg body weight of a human and non-human animal, preferably from about 10 mg to about 10 g per kg of body weight of a human and non-human animal and most preferably from about 50 mg to about 2 g per kg of body weight of a human and non-human animal.

Other Aspects of the Invention

The present invention also provides a combination (for example for the treatment of mitochondrial dysfunction) of a compound of formula (I) or a pharmaceutically acceptable form thereof as hereinbefore defined and one or more agents independently selected from:

Quinone derivatives, e.g. Ubiquinone, Idebenone, MitoQ

Vitamins e.g. Tocopherols, Tocotrienols and Trolox (Vitamin E), Ascorbate (C), Thiamine (B1), Riboflavin (B2), Nicotinamide (B3), Menadione (K3), Antioxidants in addition to vitamins e.g. TPP-compounds (MitoQ), Sk-compounds, Epicatechin, Catechin, Lipoic acid, Uric acid, Melatonin Dichloroacetate Methylene blue L-arginine Szeto-Schiller peptides Creatine Benzodiazepines Modulators of PGC-1α

Ketogenic diet

Other aspects appear from the appended claims. All details and particulars apply mutatis mutandis to these aspects.

DEFINITIONS

Amino

Amino means $NH_2$. Amino includes substituted amino. Substituted amino means NHR or $NR^2R^3$ where $R^2$ and $R^3$ are independent substituents or where $NR^2R^3$ forms an optionally substituted 4 to 7 membered non-aromatic heterocyclic ring optionally containing a second heteroatom ring member selected from O, N and S and oxidised forms thereof.

Exemplary substituted amino groups include $NMe_2$, $NEt_2$, piperidinyl, piperazinyl, morpholino, N-cyclohexyl, where the rings may be further substituted.

Alkyl

Alkyl means an aliphatic hydrocarbon group. The alkyl group may be straight or branched or cyclic. "Branched" means that at least one carbon branch point is present in the group. Thus, for example, tert-butyl and isopropyl are both branched groups. The alkyl group may be a lower alkyl group. "Lower alkyl" means an alkyl group, straight or branched, having 1 to about 6 carbon atoms, e.g. 2, 3, 4, 5 or 6 carbon atoms.

Exemplary alkyl groups include methyl, ethyl, n-propyl, i-propyl, n-butyl, t-butyl, s-butyl, n-pentyl, 2-pentyl, 3-pentyl, n-hexyl, 2-hexyl, 3-hexyl, n-heptyl, 2-heptyl, 3-heptyl, 4-heptyl, 2-methyl-but-1-yl, 2-methyl-but-3-yl, 2-methyl-pent-1-yl, 2-methyl-pent-3-yl.

The alkyl group may be optionally substituted, e.g. as exemplified below.

The term alkyl also includes aliphatic hydrocarbon groups such as alkenyl, and alkylidene and cycloalkyl, cycloalkylidene, heterocycloalkyl and heterocycloalkylidene groups, which may be further substituted.

Alkenyl

Alkenyl means an unsaturated aliphatic hydrocarbon group. The unsaturation may include one or more double bond, one or more triple bond or any combination thereof. The alkenyl group may be straight or branched. "Branched" means that at least one carbon branch point is present in the group. Any double bond may, independently of any other double bond in the group, be in either the (E) or the (Z) configuration.

The alkenyl group may be a lower alkenyl group. "Lower alkenyl" means an alkenyl group, straight or branched, having 2 to 6 carbon atoms, e.g. 2, 3, 4, 5 or 6 carbon atoms.

Exemplary alkenyl groups include ethenyl, n-propenyl, i-propenyl, but-1-en-1-yl, but-2-en-1-yl, but-3-en-1-yl, pent-1-en-1-yl, pent-2-en-1-yl, pent-3-en-1-yl, pent-4-en-1-yl, pent-1-en-2-yl, pent-2-en-2-yl, pent-3-en-2-yl, pent-4-en-2-yl, pent-1-en-3-yl, pent-2-en-3-yl, pentadien-1-yl, pentadien-2-yl, pentadien-3-yl. Where alternative (E) and (Z) forms are possible, each is to be considered as individually identified.

The alkenyl group may be optionally substituted, e.g. as exemplified below. Alkenyl includes cyano.

Alkylidene

Alkylidene means any alkyl or alkenyl group linked to the remainder of the molecule via a double bond. The definitions and illustrations provided herein for alkyl and alkenyl groups apply with appropriate modification also to alkylidene groups.

Cycloalkyl

Cycloalkyl means a cyclic non-aromatic hydrocarbon group. The cycloalkyl group may include non-aromatic unsaturation. The cycloalkyl group may have 3 to 6 carbon atoms, e.g. 3, 4, 5 or 6 carbon atoms. Exemplary cycloalkyl groups include cyclopropyl, cyclobutyl, cyclopentyl, cyclohexyl, cyclopentenyl, cyclohexenyl.

The cycloalkyl group may be optionally substituted, as defined below, e.g. as exemplified below. Exemplary substituted cycloalkyl groups include mono- or poly-alkyl-substituted cycloalkyl groups such as 1-methylcyclopropyl, 1-methylcyclobutyl, 1-methylcyclopentyl, 1-methylcyclohexyl, 2-methylcyclopropyl, 2-methylcyclobutyl, 2-methylcyclopentyl, 2-methylcyclohexyl, 1,2-dimethylcyclohexyl or 1,3-dimethylcyclohexyl.

Cycloalkylidene Group

Cycloalkylidene means any cycloalkyl group linked to the remainder of the molecule via a double bond. The definitions and illustrations provided herein for cycloalkyl groups apply with appropriate modification also to cycloalkylidene groups.

Heterocycloalkyl

Heterocycloalkyl group means a non-aromatic cyclic group which contains one or more heteroatoms in the ring. The heterocycloalkyl group may contain O, N or S atoms. The heterocycloalkyl group may be fully saturated or partially unsaturated. The heterocycloalkyl group is typically monocyclic or bicyclic, and more usually is monocyclic.

Exemplary heterocycloalkyl groups include azetidinyl, pyrrolidinyl, piperidinyl, azepinyl, diazepinyl, dihydrofuranyl (e.g. 2,3-dihydrofuranyl, 2,5-dihydrofuranyl), 4,5-dihydro-1H-maleimido, dioxolanyl, 2-imidazolinyl, imidazolidinyl, isoxazolidinyl, morpholinyl, oxazolidinyl, piperazinyl, pyrrolidinonyl, 2-pyrrolinyl, 3-pyrrolinyl, sulfolanyl, 3-sulfolenyl, tetrahydrofuranyl, thiomorpholinyl, dihydropyranyl (e.g. 3,4-dihydropyranyl, 3,6-dihydropyranyl), dioxanyl, hexahydropyrimidinyl, 2-pyrazolinyl, pyrazolidinyl, pyridazinyl, 4H-quinolizinyl, quinuclinyl, tetrahydropyranyl, 3,4,5,6-tetrahydropyridinyl, 1,2,3,4-tetrahydropyrimidinyl, 3,4,5,6-tetrahydropyrimidinyl, tetrahydrothiophenyl, tetramethylenesulfoxide, thiazolidinyl, 1,3,5-triazinanyl, 1,2,4-triazinanyl, hydantoinyl, and the like. The point of attachment may be via any atom of the ring system.

Heterocycloalkylidene Group

Heterocycloalkylidene means any heterocycloalkyl group linked to the remainder of the molecule via a double bond. The definitions and illustrations provided herein for heterocycloalkyl groups apply with appropriate modification also to heterocycloalkylidene groups.

Optionally Substituted

"Optionally substituted" as applied to any group means that the said group may if desired be substituted with one or more substituents, which may be the same or different. 'Optionally substituted alkyl' includes both 'alkyl' and 'substituted alkyl'. Examples of suitable substituents for "substituted" and "optionally substituted" moieties include halo (fluoro, chloro, bromo or iodo), $C_{1-6}$ alkyl, $C_{3-6}$ cycloalkyl, hydroxy, $C_{1-6}$ alkoxy, cyano, amino, nitro, $C_{1-6}$ alkylamino, $C_{2-6}$ alkenylamino, di-$C_{1-6}$ alkylamino, $C_{1-6}$ acylamino, di-$C_{1-6}$ acylamino, $C_{1-6}$ aryl, $C_{1-6}$ arylamino, $C_{1-6}$ aroylamino, benzylamino, $C_{1-6}$ arylamido, carboxy, $C_{1-6}$ alkoxycarbonyl or ($C_{1-6}$ aryl)($C_{1-10}$ alkoxy)carbonyl, carbamoyl, mono-$C_{1-6}$ carbamoyl, di-$C_{1-6}$ carbamoyl or any of the above in which a hydrocarbyl moiety is itself substituted by halo, cyano, hydroxy, $C_{1-2}$ alkoxy, amino, nitro, carbamoyl, carboxy or $C_{1-2}$ alkoxycarbonyl. In groups containing an oxygen atom such as hydroxy and alkoxy, the oxygen atom can be replaced with sulphur to make groups such as thio (SH) and thio-alkyl (S-alkyl). Optional substituents therefore includes groups such as S-methyl. In thio-alkyl groups, the sulphur atom may be further oxidised to make a sulfoxide or sulfone, and thus optional substituents therefore includes groups such as S(O)-alkyl and S(O)$_2$-alkyl.

Substitution may take the form of double bonds, and may include heteroatoms. Thus an alkyl group with a carbonyl (C=O) instead of a CH$_2$ can be considered a substituted alkyl group.

Substituted groups thus include for example CFH$_2$, CF$_2$H, CF$_3$, CH$_2$NH$_2$, CH$_2$OH, CH$_2$CN, CH$_2$SCH$_3$, CH$_2$O CH$_3$, OMe, OEt, Me, Et, —OCH$_2$O—, CO$_2$Me, C(O)Me, i-Pr, SCF$_3$, SO$_2$Me, NMe$_2$, CONH$_2$, CONMe$_2$ etc. In the case of aryl groups, the substitutions may be in the form of rings from adjacent carbon atoms in the aryl ring, for example cyclic acetals such as O—CH$_2$—O.

EXAMPLES

The invention will now be illustrated by the following non-limiting Examples in which, unless stated otherwise:
(i) when given, $^1$H NMR spectra were recorded on Bruker Avance 300 (300 MHz) or Bruker Avance 400 (400 MHz). Either the central peaks of the chloroform-d (CDCl$_3$; $\delta_H$ 7.27 ppm), dimethylsulfoxide-d$_6$ (d$_6$-DMSO; $\delta_H$ 2.50 ppm) or methanol-d$_4$ (CD$_3$OD; $\delta_H$ 3.31 ppm), or an internal standard of tetramethylsilane (TMS; $\delta_H$ 0.00 ppm) were used as references;

(ii) Mass spectra were recorded on an Agilent MSD (+ve and −ve electrospray) or a Fisons Instrument VG Platform following analytical HPLC. Where values for m/z are given, generally only ions which indicate the parent mass are reported, and the mass ions quoted are the positive and negative mass ions: $[M+H]^+$ or $[M-H]^-$;

(iii) The title and subtitle compounds of the examples and preparations were named using AutoNom.

(iv) Unless stated otherwise, starting materials were commercially available. All solvents and commercial reagents were of laboratory grade and were used as received. All operations were carried out at ambient temperature, i.e. in the range 16 to 28° C. and, where appropriate, under an atmosphere of an inert gas such as nitrogen;

(v) The following abbreviations are used:

| | |
|---|---|
| DCM | Dichloromethane |
| DIPEA | N,N-Diisopropylethylamine |
| DMF | N,N-Dimethylformamide |
| DMSO | Dimethyl sulfoxide |
| HPLC | High Performance Liquid Chromatography |
| g | Gram(s) |
| h | Hour(s) |
| LCMS | Liquid Chromatography - Mass Spectroscopy |
| MPLC | Medium Pressure Liquid Chromatography |
| mmol | millimole |
| TFA | Trifluoroacetic acid |

Example 1

Succinic Acid bis-(2,2-dimethyl-propionyloxymethyl)ester

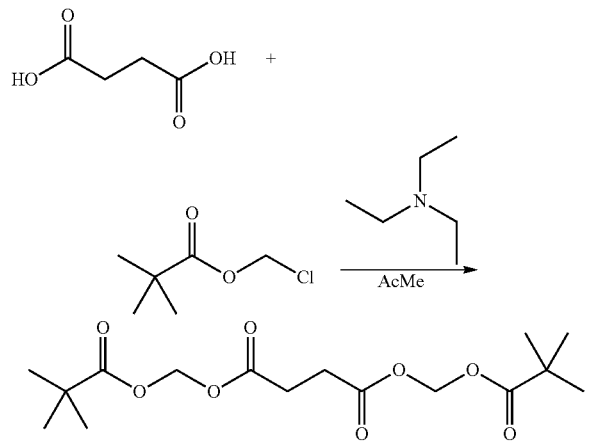

Succinic acid (1.2 g, 10 mmol) and chloromethyl pivalate (5.8 mL, 40 mmol) were added to acetone (4 mL) and the mixture cooled in ice. Triethylamine (3.3 mL, 24 mmol) was added portion-wise and the solution stirred overnight at room temperature. The mixture was concentrated and partitioned between water and ethyl acetate. The ethyl acetate solution was washed with water then sodium bicarbonate solution. It was treated with decolourising charcoal, dried over potassium carbonate and concentrated to an oil. Purification by MPLC chromatography (basic alumina, 10% ethyl acetate/90% cyclohexane) afforded 0.18 g succinic acid bis-(2,2-dimethyl-propionyloxymethyl) ester as an oil. $^1$H NMR (CDCl$_3$, ppm) δ 1.23 (s, 18H), 2.71 (s, 4H), 5.77 (s, 4H).

Example 2

Succinic Acid 2,2-dimethyl-propionyloxymethyl Ester Methyl Ester

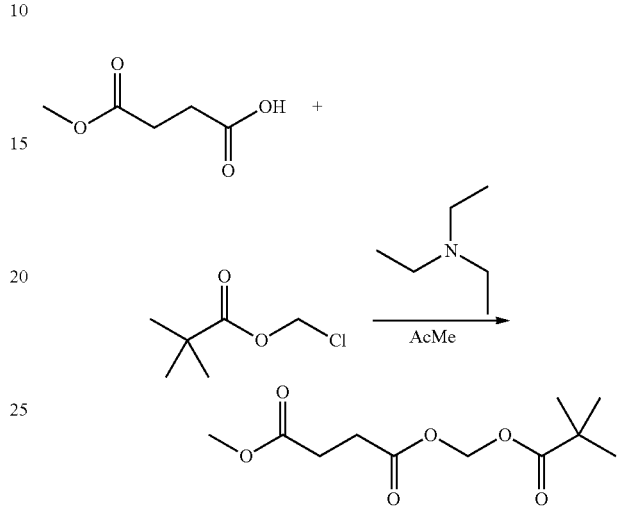

Methyl succinate (1.3 g, 10 mmol) and chloromethyl pivalate (2.9 mL, 20 mmol) were added to acetone (2 mL) and the mixture cooled in ice. Triethylamine (2.0 mL, 14 mmol) was added portion-wise and the solution stirred overnight at room temperature. The mixture was concentrated and partitioned between water and ethyl acetate. The ethyl acetate solution was washed with water then sodium bicarbonate solution, dried over potassium carbonate and concentrated to give 2.4 g succinic acid 2,2-dimethyl-propionyloxymethyl ester methyl ester as an oil. $^1$H NMR (CDCl$_3$, ppm) δ 1.23 (s, 9H), 2.68 (m, 4H), 3.71 (s, 3H), 5.78 (s, 2H).

Example 3

Succinic Acid Diacetoxymethyl Ester

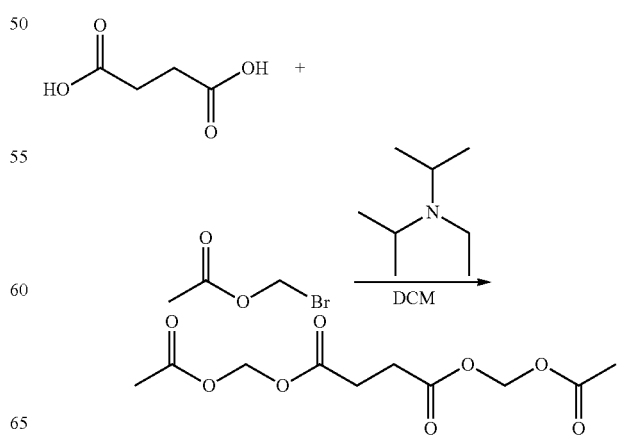

Succinic acid (58.6 g, 0.496 mol) was added to dichloromethane (2 L) and the mixture cooled to 0° C. Diisopropylethylamine (201 mL, 1.154 mol) was added during 20 minutes followed by bromomethyl acetate (159.4 g, 1.042 mol) during 30 minutes and the solution stirred overnight under an atmosphere of nitrogen. The solution was cooled to 0° C. and washed successively with 1 L of cold 1% hydrochloric acid, 0.6% hydrochloric acid and water (×3). The solution was treated with decolourizing charcoal, dried with magnesium sulphate and concentrated to an oil which was crystallized from diethyl ether (200 mL)/isohexane (10 mL) to afford 92 g of succinic acid diacetoxymethyl ester as a white solid. $^1$H NMR (CDCl$_3$, ppm) δ 2.13 (s, 6H), 2.72 (s, 4H), 5.76 (s, 4H). A further 8 g of pure material was obtained from concentration of the liquors.

Example 4

Succinic Acid Acetoxymethyl Ester Methyl Ester

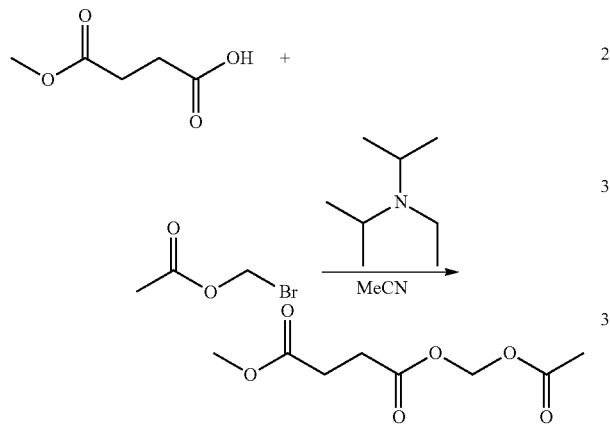

Methyl succinate (2.0 g, 15.1 mmol) was dissolved in acetonitrile (200 mL) and bromomethyl acetate (1.65 mL, 16.8 mmol) was added. The solution was cooled in cold water and diisopropylethylamine (3.16 mL, 18.2 mmol) was added. The solution was allowed to warm and stirred at room temperature for 70 minutes. The solution was poured into ice/water (400 mL) and extracted with ethyl acetate. This ethyl acetate solution was washed with water, 1% hydrochloric acid, sodium bicarbonate solution and brine. It was dried with magnesium sulphate and concentrated to an oil. Purification by MPLC (SiO$_2$, isohexane→20% ethyl acetate/80% isohexane) gave 0.91 g succinic acid acetoxymethyl ester methyl ester. $^1$H NMR (CDCl$_3$, ppm) δ 2.13 (s, 3H), 2.69 (m, 4H), 3.71 (s, 3H), 5.77 (s, 2H).

Example 5

Succinic Acid bis-(1-acetoxy-ethyl)ester

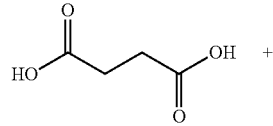

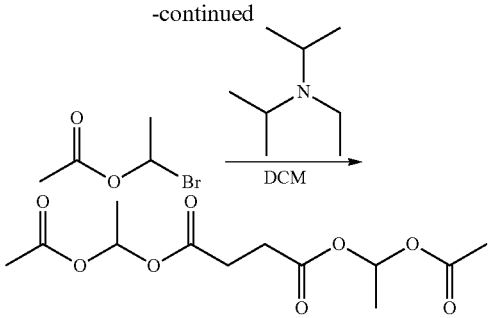

Succinic acid (58.6 g, 0.496 mol) was added to dichloromethane (2 L) and the mixture cooled to 0° C. Diisopropylethylamine (201 mL, 1.154 mol) was added during 20 minutes followed by 1-bromoethyl acetate (159.4 g, 1.042 mol) during 30 minutes and the solution stirred overnight under an atmosphere of nitrogen. The solution was cooled to 0° C. and washed successively with cold (1.5 L quantities) of water, 1% hydrochloric acid (twice), sodium bicarbonate solution and water. The solution was dried with magnesium sulphate and concentrated to an oil which was crystallized from t-butylmethyl ether to afford 41 g of succinic acid diacetoxymethyl ester as a white solid. $^1$H NMR (CDCl$_3$, ppm) δ 1.48 (d, J=5.4 Hz, 6H), 2.07 (s, 6H), 2.66 (m, 4H), 6.87 (q, J=5.5 Hz, 2H).

Example 6

Succinic Acid 1-Acetoxy-Ethyl Ester Methyl Ester

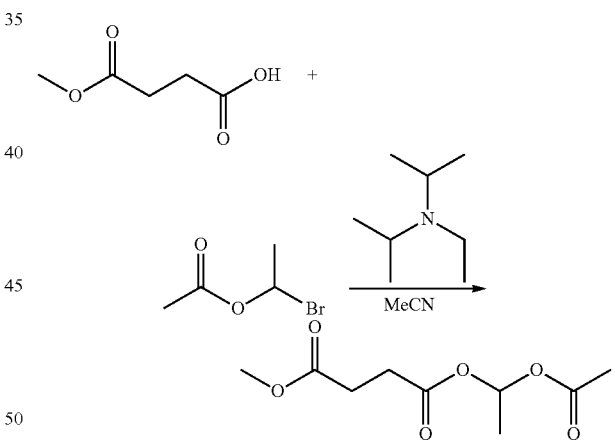

Methyl succinate (2.46 g, 18.6 mmol) was dissolved in acetonitrile (350 mL) and the solution cooled to −5° C. 1-Bromoethyl acetate (3.3 g, 19.8 mmol) and then diisopropylethylamine (4.0 mL, 23.3 mmol) were added. The solution was allowed to warm and stirred at room temperature for 3 days. The solution was cooled and partitioned between cold water and ethyl acetate. This ethyl acetate solution was washed with 1% hydrochloric acid, sodium bicarbonate solution then twice with water. The solution was dried with magnesium sulphate and concentrated to an oil.

Purification by MPLC (SiO$_2$, isohexane→10% ethyl acetate/90% isohexane) gave 1.9 g succinic acid 1-acetoxy-ethyl ester methyl ester as an oil. $^1$H NMR (CDCl$_3$, ppm) δ 1.48 (d, J=5.3 Hz, 3H), 2.07 (s, 3H), 2.65 (m, 4H), 3.70 (s, 3H), 6.86 (q, J=5.3 Hz, 1H).

Example 7

Succinic Acid bis-(1-acetoxy-propyl)ester

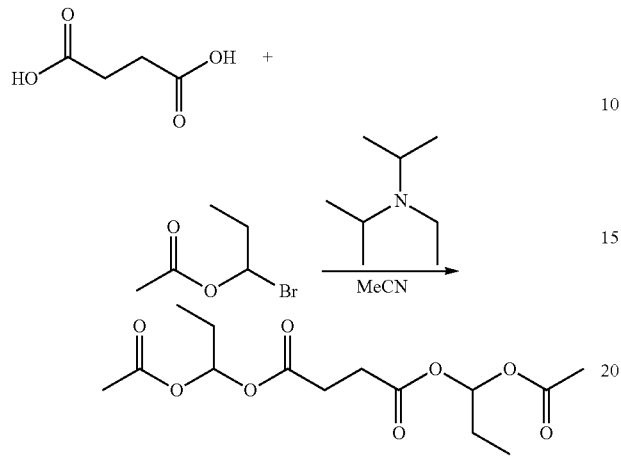

Succinic acid (2.0 g, 16.9 mmol) was dissolved in acetonitrile (350 mL) and the solution cooled to −5° C. 1-Bromopropyl acetate (6.7 g, 37.0 mmol) and then diisopropylethylamine (7.3 mL, 41.9 mmol) were added. The solution was stirred at room temperature for 3 days. The solution was cooled and partitioned between cold water and ethyl acetate. This ethyl acetate solution was washed with cold 1% hydrochloric acid, sodium bicarbonate solution then water. It was dried with magnesium sulphate and concentrated to an oil. Purification by MPLC (SiO$_2$, isohexane→10% ethyl acetate/90% isohexane) gave 0.85 g succinic acid bis-(1-acetoxypropyl) ester as an oil. $^1$H NMR (CDCl$_3$, ppm) δ 0.97 (t, J=7.6 Hz, 6H), 1.81 (m, 4H), 2.09 (s, 6H), 2.68 (m, 4H), 6.77 (t, J=5.6 Hz, 2H).

Example 8

Succinic Acid bis-(1-propionyloxy-ethyl)ester

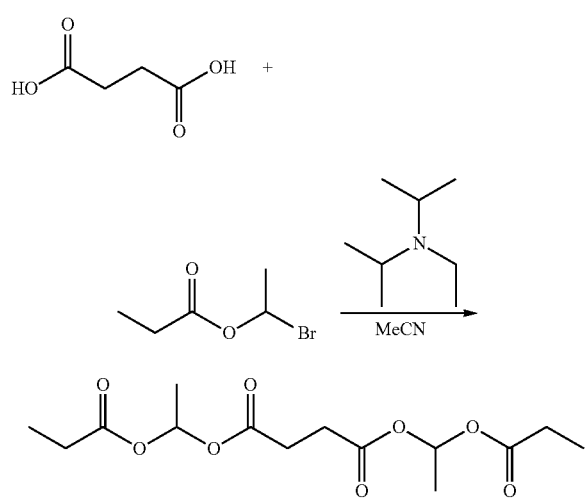

Succinic acid (2.0 g, 16.9 mmol) was dissolved in acetonitrile (350 mL) and the solution cooled to −5° C. 1-Bromoethyl propionate (6.7 g, 37.0 mmol) and then diisopropylethylamine (7.3 mL, 41.9 mmol) were added. The solution was allowed to warm and stirred at room temperature overnight. The solution was cooled and partitioned between cold water and ethyl acetate. This ethyl acetate solution was washed with cold 1% hydrochloric acid, sodium bicarbonate solution and then twice with water. It was dried with magnesium sulphate and concentrated to an oil. Purification by MPLC (SiO$_2$, isohexane→10% ethyl acetate/90% isohexane) gave 3.1 g succinic acid bis-(1-propionyloxy-ethyl) ester as an oil. $^1$H NMR (CDCl$_3$, ppm) δ 1.15 (t, J=7.5 Hz, 6H), 1.49 (d, J=5.4 Hz, 6H), 2.36 (q, J=7.6 Hz, 4H), 2.66 (m, 4H), 6.90 (t, J=5.4 Hz, 2H).

Example 9

1,3,5,7-Tetraoxa-cycloundecane-8,11-dione

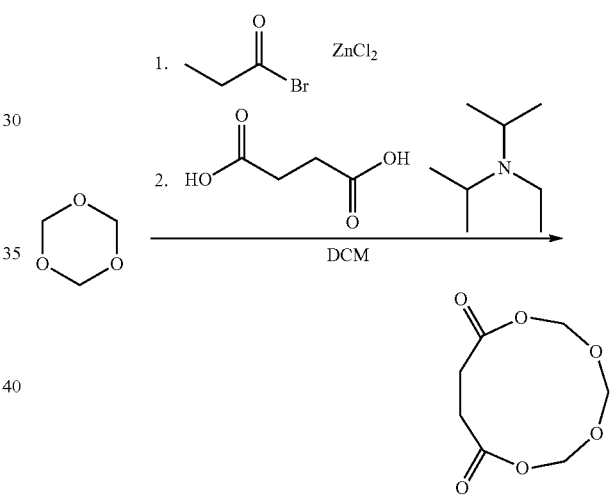

Propionyl bromide (8 mL, 89 mmol) was dissolved in dichloromethane (20 mL) and the solution cooled to −5° C. Zinc chloride (35 mg, 0.26 mmol) was added followed by trioxane (2.67 g, 29.7 mmol) portion wise during 30 minutes. The solution was stirred at 0° C. for 1 hour and then at room temperature for a further hour. The solution was washed three times with cold water, dried with magnesium sulphate and concentrated to an oil. The crude product from this reaction (7.0 g) was added to a mixture of succinic acid (2.34 g, 19.8 mmol) and diisopropylethylamine (8.3 mL, 43.7 mmol) in dichloromethane (350 mL) cooled to −5° C. The solution was stirred at room temperature overnight and then washed with cold 1% hydrochloric acid, sodium bicarbonate solution followed by water (×3). The combined extracts were dried with magnesium sulphate and concentrated to an oil. Trituration with diethyl ether afforded 0.24 g 1,3,5,7-tetraoxa-cycloundecane-8,11-dione as a white solid. $^1$H NMR (CDCl$_3$, ppm) δ 2.66 (s, 4H), 5.00 (s, 2H), 5.43 (s, 4H).

Example 10

Succinic Acid Acetoxymethyl Ester Diethylcarbamoylmethyl Ester i) 2-Chloro-N,N-diethyl-acetamide

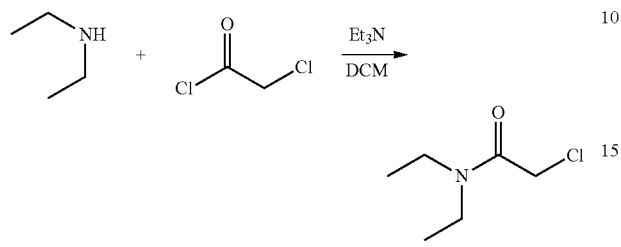

Diethylamine (10.0 mL, 97 mmol) and triethylamine (13.5 mL, 97 mmol) were diluted in dichloromethane (30 mL), the solution was cooled to 0° C. and chloroacetyl chloride (7.7 mL, 97 mmol) in DCM (10 ml) was added during 10 minutes, and the solution allowed to warm to room temperature and stirred overnight under an atmosphere of nitrogen. The solution was washed with water (2×10 mL). The organics were combined and the volatiles were removed in vacuo. The residue was purified by silica gel chromatography with a continuous gradient of iso-hexane/ethyl acetate 1:0 to 1:1 to afford the title compound (12.3 g) as a clear oil. $^1$H NMR (300 MHz, CDCl$_3$) δ 1.11 (t, J=7.1 Hz, 3H), 1.21 (t, J=7.1 Hz, 3H), 3.35 (quint, J=6.9 Hz, 4H), 4.03 (s, 2H). LCMS (m/z) 150.1-152.1 [M+H]$^+$.

ii) Succinic Acid Tert-Butyl Ester Diethylcarbamoylmethyl Ester

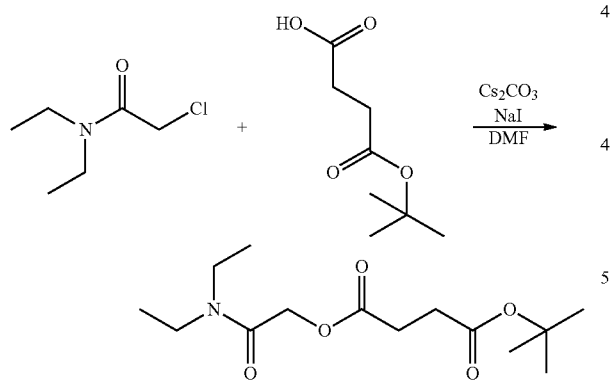

2-Chloro-N,N-diethyl-acetamide (Example 10, step (i), 1.71 g, 11.48 mmol), Succinic acid mono-tert-butyl ester (2.00 g, 11.48 mmol), caesium carbonate (2.67 g, 8.21 mmol), and sodium iodide (171 mg, 1.14 mmol), were suspended in DMF (20 mL) and the suspension stirred at 80° C. for 3 hours under an atmosphere of nitrogen. The suspension was cooled down to room temperature, diluted with ethyl acetate (40 mL) and washed with water (3×10 mL). The organics were combined and the volatiles were removed in vacuo. The residue was purified by silica gel chromatography with a continuous gradient of iso-hexane/ethyl acetate 1:0 to 0:1 to afford the title compound (3.29 g) as a clear oil.

$^1$H NMR (300 MHz, CDCl$_3$) δ 1.13 (t, J=7.1 Hz, 3H), 1.22 (t, J=7.1 Hz, 3H), 1.44 (s, 9H), 2.55-2.77 (m, 4H), 3.24 (q, J=7.1 Hz, 2H), 3.38 (q, J=7.1 Hz, 2H), 4.73 (s, 2H). LCMS (m/z) 288.1 [M+H], Tr=2.07 min.

iii) Succinic Acid Monodiethylcarbamoylmethyl Ester

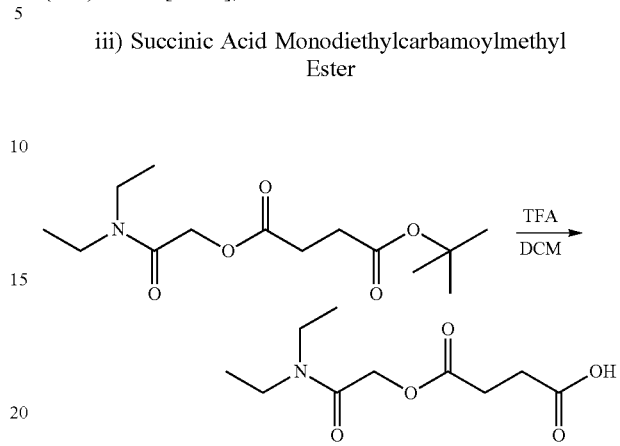

Succinic acid tert-butyl ester diethylcarbamoylmethyl ester (Example 10, step (ii), 3.29 g, 11.48 mmol) was dissolved in DCM (15 mL), the solution was cooled to 0° C. and trifluoroacetic acid (5 mL) was added. The solution was allowed to warm to room temperature and stirred overnight under an atmosphere of nitrogen. The volatiles were removed in vacuo the residue azeotroped with toluene (3×20 mL) to afford the title compound (3.19 g) as a clear oil. $^1$H NMR (300 MHz, CDCl$_3$) δ 1.16 (t, J=7.1 Hz, 3H), 1.26 (t, J=7.1 Hz, 3H), 2.65-2.85 (m, 4H), 3.30 (q, J=7.1 Hz, 2H), 3.42 (q, J=7.1 Hz, 2H), 4.79 (s, 2H), 10.43 (br, 1H). LCMS (m/z) 232.1 [M+H]$^+$, 230.1 [M−H]$^-$.

Example 10

Succinic Acid Acetoxymethyl Ester Diethylcarbamoylmethyl Ester

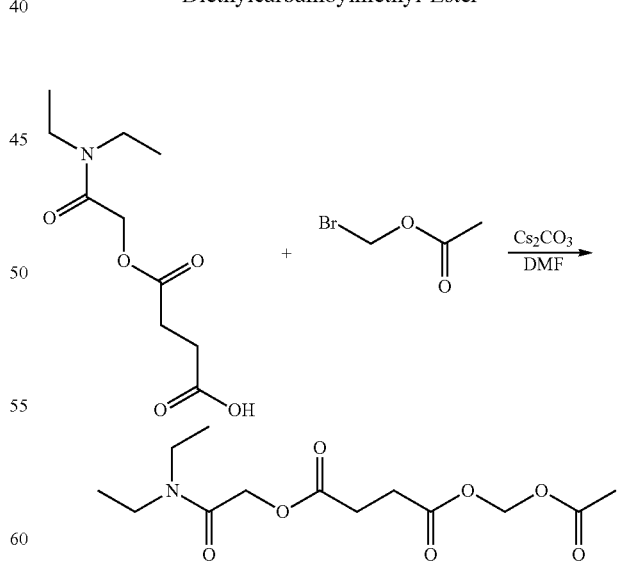

Succinic acid monodiethylcarbamoylmethyl ester (Example 10, step (iii), 850 mg, 3.68 mmol), acetic acid bromomethyl ester (671 mg, 4.42 mmol), caesium carbonate (1.78 g, 5.47 mmol), were suspended in DMF (10 mL) and the suspension stirred at 80° C. for 2 hours under an atmosphere of nitrogen. The suspension was cooled to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (334 mg) as a white solid. $^1$H NMR (300 MHz, CDCl$_3$) δ 1.14 (t, J=7.1 Hz, 3H), 1.23 (t, J=7.1 Hz, 3H), 2.12 (s, 3H), 2.67-2.87 (m, 4H), 3.25 (q, J=7.1 Hz, 2H), 3.39 (q, J=7.1 Hz, 2H), 4.75 (s, 2H), 5.76 (s, 2H). LCMS (m/z) 304.0 [M+H]$^+$.

Example 11

Succinic Acid Diethylcarbamoylmethyl Ester 1-Ethoxycarbonyloxy-Ethyl Ester

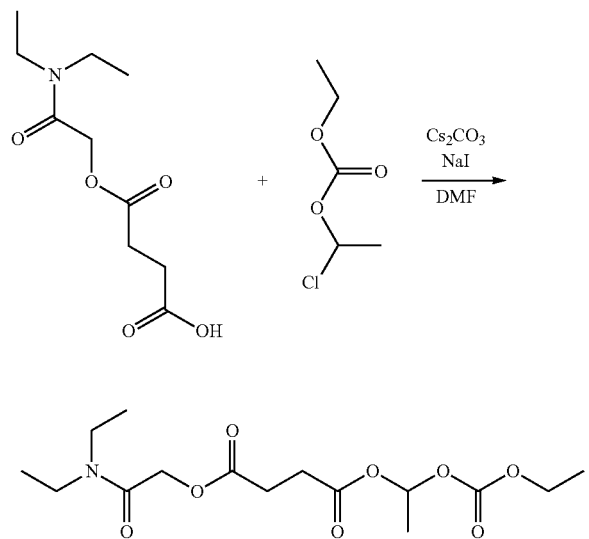

Succinic acid monodiethylcarbamoylmethyl ester (500 mg, 2.16 mmol), carbonic acid 1-chloro-ethyl ester ethyl ester (395 mg, 2.60 mmol), caesium carbonate (625 mg, 1.92 mmol), sodium iodide (32 mg, 0.21 mmol) were suspended In DMF (10 mL) and the suspension stirred at 80° C. for 3 hours under an atmosphere of nitrogen. The suspension was cooled down to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (585 mg) as a clear oil. $^1$H NMR (300 MHz, CDCl$_3$) δ 1.14 (t, J=7.1 Hz, 3H), 1.23 (t, J=7.1 Hz, 3H), 1.32 (t, J=7.1 Hz, 3H), 1.53 (d, J=5.5 Hz 3H), 2.67-2.87 (m, 4H), 3.25 (q, J=7.1 Hz, 2H), 3.39 (q, J=7.1 Hz, 2H), 4.22 (q, J=7.1 Hz, 2H), 4.74 (d, J=8.03 Hz, 2H), 6.77 (q, J=5.5 Hz, 1H). LCMS (m/z) 348.0 [M+H]$^+$.

Example 12

Succinic Acid 1-Acetoxy-Ethyl Ester Diethylcarbamoylmethyl Ester

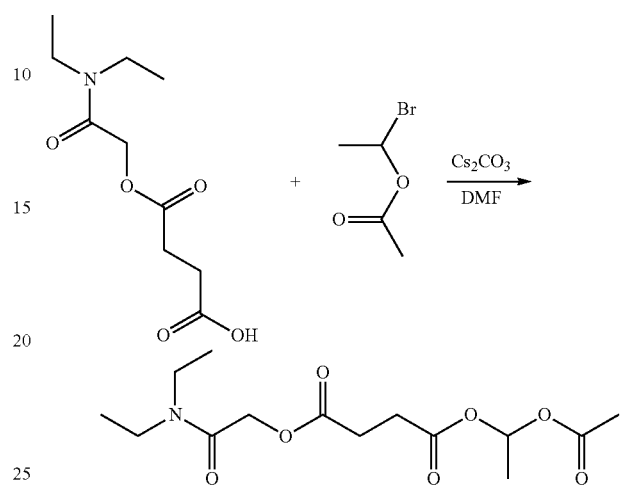

Succinic acid monodiethylcarbamoylmethyl ester (500 mg, 2.16 mmol), acetic acid 1-bromo-ethyl ester (434 mg, 2.60 mmol), caesium carbonate (625 mg, 1.92 mmol) were suspended in DMF (10 mL) and the suspension stirred at 70° C. for 2 hours under an atmosphere of nitrogen. The suspension was cooled down to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (352 mg) as a clear oil. $^1$H NMR (300 MHz, CDCl$_3$) δ 1.14 (t, J=7.1 Hz, 3H), 1.23 (t, J=7.1 Hz, 3H), 1.48 (d, J=5.5 Hz, 3H), 2.07 (s, 3H), 2.66-2.85 (m, 4H), 3.25 (q, J=7.1 Hz, 2H), 3.39 (q, J=7.1 Hz, 2H), 4.74 (d, J=5.1 Hz, 2H), 6.87 (q, J=5.5 Hz, 1H). LCMS (m/z) 318.1 [M+H]$^+$.

Example 13

Succinic Acid 1-Acetoxy-Ethyl Ester Acetoxymethyl Ester i) Succinic Acid 1-Acetoxy-Ethyl Ester Tert-Butyl Ester

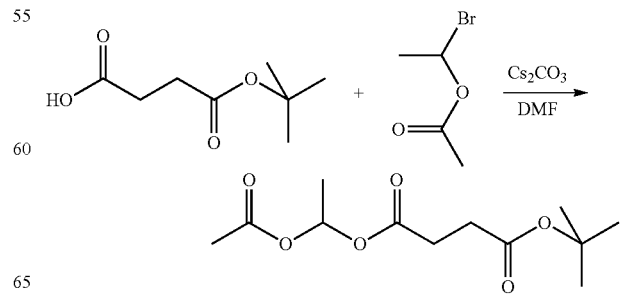

Succinic acid mono-tert-butyl ester (2.0 g, 11.48 mmol), acetic acid 1-bromo-ethyl ester (1.9 g, 11.48 mmol), caesium carbonate (2.6 g, 8.0 mmol) were suspended in DMF (20 mL) and the suspension stirred at 60° C. for 2 hours under an atmosphere of nitrogen. The suspension was cooled to room temperature, diluted with ethyl acetate (50 mL) and washed with water (3×10 mL). The organics were combined and the volatiles were removed in vacuo. The residue was purified by silica gel chromatography with a continuous gradient of iso-hexane/ethyl acetate 1:0 to 0:1 to afford the title compound (2.21 g) as a clear oil. $^1$H NMR (300 MHz, CDCl$_3$) δ 1.45 (s, 9H), 1.48 (d, J=5.5 Hz, 3H), 2.07 (s, 3H), 2.50-2.65 (m, 4H), 6.88 (q, J=5.5 Hz, 1H).

ii) Succinic Acid mono-(1-acetoxy-ethyl)ester

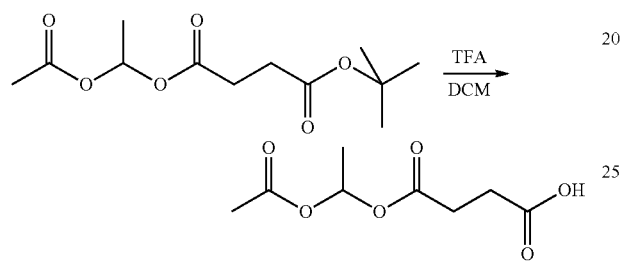

Succinic acid 1-acetoxy-ethyl ester tert-butyl ester (Example 13, step (i), 2.21 g, 8.49 mmol) was dissolved in DCM (10 mL), the solution was cooled to 0° C. and trifluoroacetic acid (2 mL) was added. The solution was allowed to warm to room temperature and stirred for 3 hours under an atmosphere of nitrogen. The volatiles were removed in vacuo the residue azeotroped with toluene (3×20 mL) to afford the title compound (1.52 g) as a clear oil. $^1$H NMR (300 MHz, CDCl$_3$) δ 1.40 (d, J=5.5 Hz, 3H), 2.03 (s, 3H), 2.40-2.60 (m, 4H), 6.73 (q, J=5.5 Hz, 1H), 10-14 (br, 1H).

Example 13

Succinic Acid 1-Acetoxy-Ethyl Ester Acetoxymethyl Ester

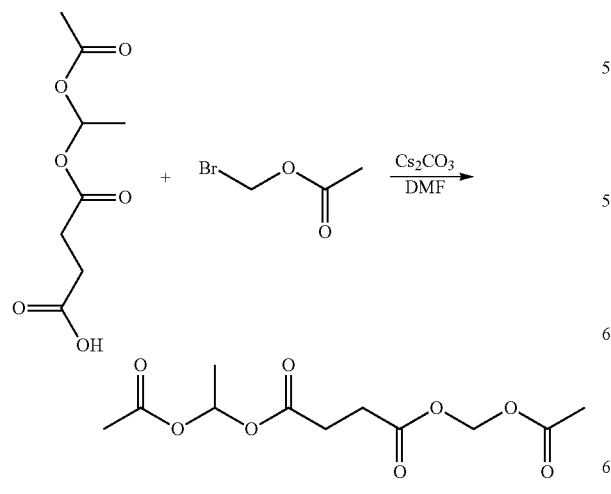

Succinic acid mono-(1-acetoxy-ethyl) ester (Example 13, step (ii), 500 mg, 2.45 mmol), acetic acid bromomethyl ester (450 mg, 2.93 mmol), caesium carbonate (712 mg, 2.19 mmol), were suspended in DMF (10 mL) and the suspension stirred at 60° C. for 3 hours under an atmosphere of nitrogen. The suspension was cooled to room temperature, diluted with ethyl acetate (30 mL) and washed with water (3×5 mL). The organics were combined and the volatiles were removed in vacuo. The residue was purified by silica gel chromatography with a continuous gradient of iso-hexane/ethyl acetate 1:0 to 0:1 to afford the title compound (267 mg) as a clear oil. $^1$H NMR (300 MHz, CDCl$_3$) δ 1.49 (d, J=5.5 Hz, 3H), 2.08 (s, 3H), 2.13 (s, 3H), 2.60-2.77 (m, 4H), 5.76 (s, 2H), 6.87 (q, J=5.5 Hz, 1H). LCMS (m/z) 277.0 [M+H]$^+$, 299 [M+Na]$^+$ Example 14

Succinic Acid bis-(2,2-dimethyl-5-oxo-[1,3]dioxolan-4-yl)ester

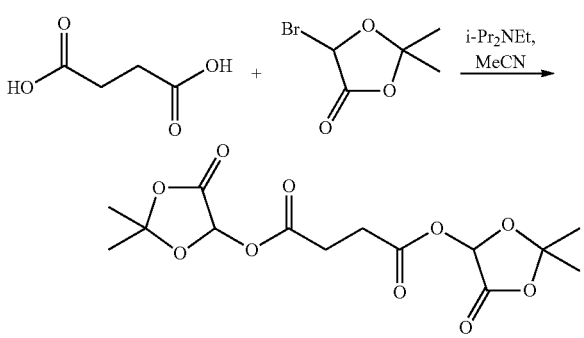

To succinic acid (2.36 g, 20 mmol) and diisopropylethylamine (8.1 mL, 46.5 mmol) in acetonitrile under an atmosphere of nitrogen and cooled in an ice bath was added 5-bromo-2,2-dimethyl-[1,3]dioxolan-4-one (8.27 g, 42.4 mmol). The mixture was allowed to warm to room temperature over 18 h. The solution was re-cooled in an ice bath, diluted with ethyl acetate and washed with 1M HCl, water, aqueous sodium hydrogen carbonate solution and water. The organic phase was dried over magnesium sulphate and concentrated to afford the title compound (3.4 g) as a white solid. $^1$H NMR (300 MHz, CDCl$_3$) δ 1.15 (m, 12H), 2.41 (m, 4), 5.77 (m, 2H).

Example 15

Succinic Acid bis-(methoxy-methoxycarbonyl-methyl)ester

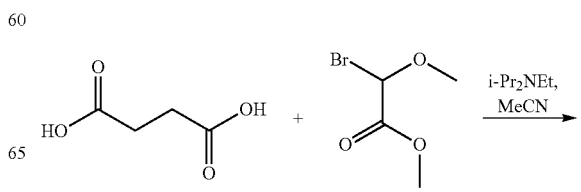

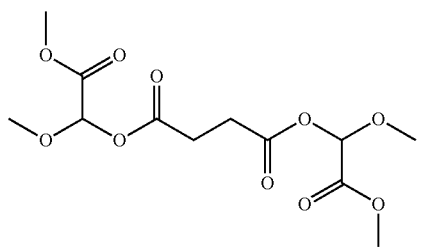

The titled compound was prepared by the method according to Example 14. $^1$H NMR (300 MHz, CDCl$_3$) δ 2.83 (m, 4H), 3.47 (s, 6H), 3.59 (s, 6H), 5.97 (s, 2H).

Example 16

Succinic Acid 1-acetoxy-ethyl Ester 1-ethoxycarbonyloxy-ethyl Ester

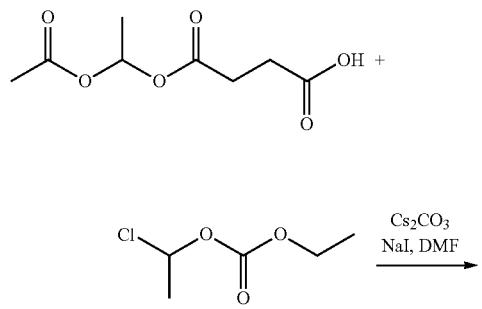

Succinic acid mono-(1-acetoxy-ethyl) ester (Example 13, step (ii), 1 g, 4.90 mmol), 1-chloroethyl ethyl carbonate (895 mg, 5.88 mmol), caesium carbonate (1.4 g, 7.35 mmol) and sodium iodide (73 mg, 0.49 mmol) were dissolved in DMF (15 mL) and the mixture heated to 80° C. for 3 hours. The mixture was allowed to cool to room temperature and then partitioned between water and ethyl acetate. The organic layer was dried over magnesium sulphate and concentrated to afford a crude residue which was purified by chromatography on silica gel chromatography with a continuous gradient of iso-hexane/ethyl acetate 1:0 to 0:1 to afford the title compound (118 mg). $^1$H NMR (300 MHz, CDCl$_3$) δ 1.31 (t, J=7.1 Hz, 3H), 1.46 (d, J=5.4 Hz, 3H), 1.51 (d, J=5.4 Hz, 3H), 2.06 (s, 3H), 2.56-2.74 (m, 4H), 4.21 (q, J=7.1 Hz, 2H), 6.76 (q, J=5.4 Hz, 1H), 6.85 (q, J=5.4 Hz, 1H).

Example 17

Succinic Acid 3-(1-acetoxy-ethoxycarbonyl)-propionyloxymethyl Ester 1-acetoxy-ethyl Ester i) Succinic Acid 3-tert-butoxycarbonyl-propionyloxymethylester tert-butyl ester

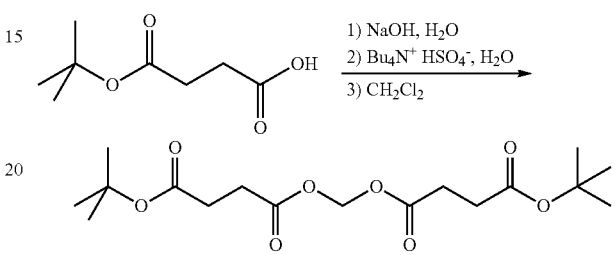

To t-butyl succinate (8.7 g, 50 mmol) was added aqueous sodium hydroxide solution (50 mL, 2M) and the mixture stirred for 10 min. Tetrabutyammonium hydrogen sulphate (17 g) was added and the mixture stirred for a further 30 min. The solution was extracted with dichloromethane (4×100 mL) and the combined extracts dried over magnesium sulphate. The dichloromethane solution was then heated at 40° C. for 5 days. The solution was allowed to cool to room temperature and washed with sulphuric acid (1M), water and sodium hydrogen carbonate solution followed by water. The organic phase was then dried and concentrated to afford the titled compound as crude product (5.7 g). $^1$H NMR (CDCl$_3$, ppm) δ 1.45 (s, 18H), 2.53-2.67 (m, 8H), 5.79 (m, 2H).

ii) Succinic Acid mono-(3-carboxy-propionyloxymethyl)ester

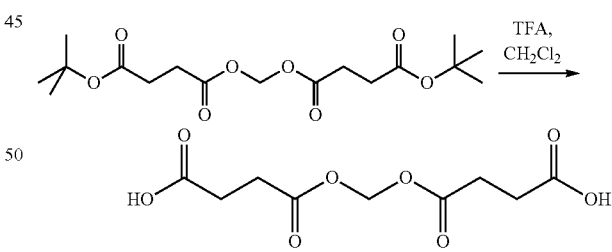

Succinic acid 3-tert-butoxycarbonyl-propionyloxymethylester tert-butyl ester (1.8 g, 7.3 mmol) was dissolved in dichloromethane (27 mL) and the mixture cooled to −78° C. under nitrogen. Trifluoroacetic acid (0.77 mL, 10 mmol) was added and the mixture allowed to warm to 4° C. after which it was maintained at 4° C. for 18 h. The mixture was evaporated and azeotroped with toluene. Analysis showed incomplete reaction so the crude mixture was subjected to the same reaction conditions for a further 4 days. The mixture was evaporated and azeotroped with toluene and used in the following step as a crude product (1.3 g). $^1$H NMR (CDCl$_3$, ppm) δ 2.52-2.64 (m, 8H), 5.71 (s, 2H).

Example 17

Succinic Acid 3-(1-acetoxy-ethoxycarbonyl)-propionyloxymethyl Ester 1-acetoxy-ethyl Ester

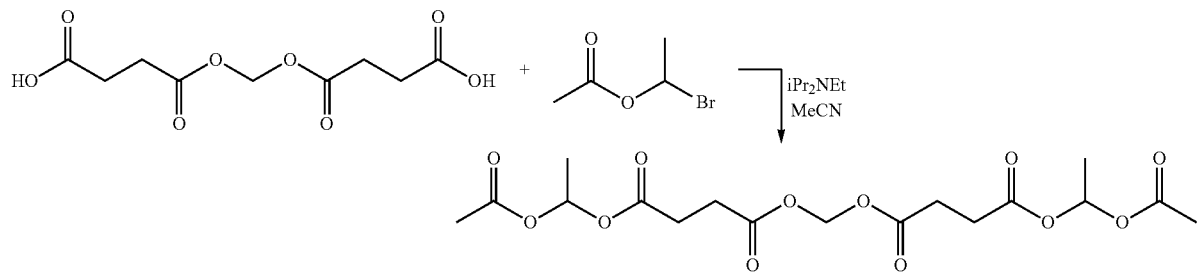

The titled compound was prepared by the method of Example 6 using succinic acid mono-(3-carboxy-propionyloxymethyl) ester (Ex 17ii, 1.3 g) and 1-bromoethyl acetate (1.8 g) to afford 240 mg of product after purification. $^1$H NMR (CDCl$_3$, ppm) δ 1.50 (d, 6H), 2.09 (s, 6H), 2.60-2.75 (m, 8H), 5.78 (s, 2H), 6.90 (q, 2H).

Example 18

Succinic Acid 3-acetoxymethoxycarbonyl-propionyloxymethyl Ester Acetoxymethyl Ester

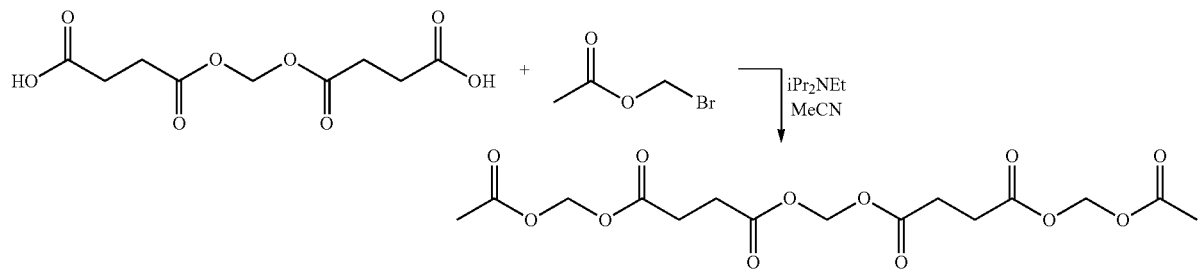

The titled compound was prepared by the method of Example 6 using succinic acid mono-(3-carboxy-propionyloxymethyl) ester (Ex 17ii, 1.0 g, 4.0 mmol) and 1-bromomethyl acetate (1.3 g, 8.5 mmol) to afford 1.4 g of product after purification. $^1$H NMR (CDCl$_3$, ppm) δ 2.15 (s, 6H), 2.73 (s, 8H), 5.72-5.82 (m, 6H).

Alternative Procedure for Example 13 Succinic Acid 1-Acetoxy-Ethyl Ester acetoxymethyl Ester i) Succinic Acid 1-acetoxy-ethyl Ester tert-butyl Ester

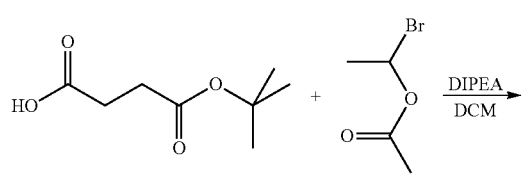

Succinic acid mono-tert-butyl ester (60.2 g, 345 mmol) was dissolved in dichloromethane (600 mL), and diisopropylethylamine (72.2 mL, 53.4 g, 414 mmol) was added. The reaction was cooled to 0° C., and 1-bromoethyl acetate (63.4 g, 380 mmol) was added dropwise. Once addition was complete, the reaction was allowed to warm to room temperature over 16 hours. The reaction was concentrated under reduced pressure. The residue was dissolved in ethyl acetate (450 mL) and washed successively with cold (400 mL quantities) of 0.5 M aqueous hydrochloric acid, aqueous saturated sodium bicarbonate solution and saturated aqueous sodium chloride solution. The organics were dried with magnesium sulphate and concentrated under reduced pressure to an oil. The oil was purified by vacuum distillation to give the sub-titled compound (75 g) as a colourless oil (vapour temperature of 150-180° C. at 1 mbar). $^1$H NMR consistent with previous material.

ii) Succinic Acid mono-(1-acetoxy-ethyl) Ester

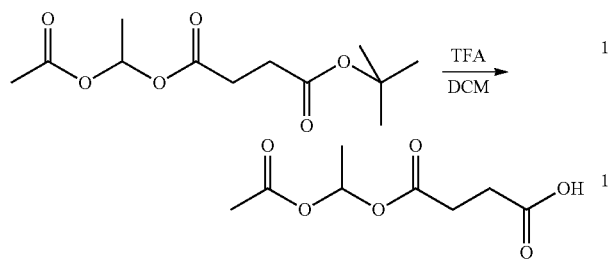

The sub-titled compound was prepared as described above in Example 13 (ii). $^1$H NMR consistent with previous material.

Example 13

Succinic Acid 1-Acetoxy-Ethyl Ester Acetoxymethyl Ester

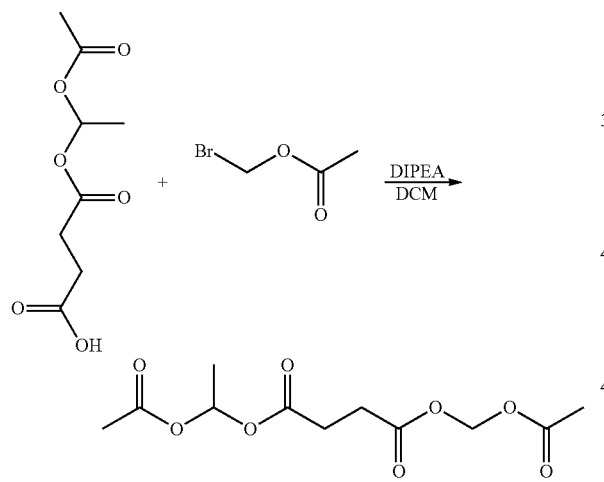

Succinic acid mono-(1-acetoxy-ethyl) ester (Example 13, step (ii), 62 g, 303 mmol) was dissolved in dichloromethane (600 mL), and diisopropylethylamine (60.1 mL, 44.6 g, 345 mmol) was added. The reaction was cooled to 0° C., and bromomethyl acetate (31.0 mL, 48.4 g, 316 mmol) was added dropwise. Once addition was complete, the reaction was allowed to warm to room temperature over 4 hours. The reaction was concentrated under reduced pressure. The residue was dissolved in ethyl acetate (450 mL) and washed successively with cold (400 mL quantities) of 0.5 M aqueous hydrochloric acid, aqueous saturated sodium bicarbonate solution and saturated aqueous sodium chloride solution. The organics were dried with magnesium sulphate and concentrated under reduced pressure to an oil. The oil was purified by vacuum distillation to give the titled compound (57.5 g) as a colourless oil (vapour temperature of 137-147° C. at 0.13 mbar). $^1$H NMR (300 MHz, CDCl$_3$) δ 1.50 (d, J=5.5 Hz, 3H), 2.09 (s, 3H), 2.13 (s, 3H), 2.66-2.72 (m, 4H), 5.77 (s, 2H), 6.88 (q, J=5.5 Hz, 1H).

Alternative Route to Example 13(ii) Succinic Acid mono-(1-acetoxy-ethyl)ester i) Succinic Acid 1-Acetoxy-Ethyl Ester Benzyl Ester

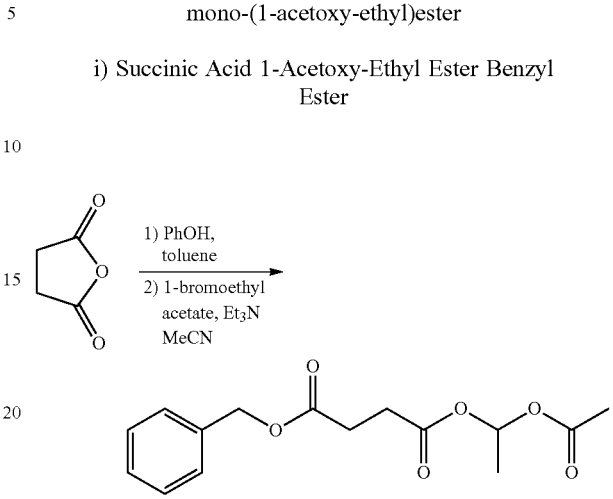

Succinic anhydride (3 g, 30 mmol) was suspended in toluene (5 mL) and benzyl alcohol (3.25 mL, 31.4 mmol) was added. The reaction was then heated to reflux for 2 hours. The reaction was concentrated under reduced pressure, and the residue was dissolved in acetonitrile (10 mL), triethylamine (5.43 mL, 39 mmol) was added, followed by dropwise addition of 1-bromoethyl acetate (5.51 g, 33 mmol) and the reaction was stirred for 2 hours at room temperature. The reaction was concentrated under reduced pressure, and the residue was partitioned between dichloromethane (20 mL) and water (20 mL). The layers were separated, and the organic phases dried with magnesium sulphate, and concentrated under reduced pressure. The product was purified by vacuum distillation to afford the sub-titled product (6.1 g) as a colourless oil (vapour temperature of 162-168° C. at 0.19 mbar). $^1$H NMR (CDCl$_3$, ppm) δ 1.47 (d, J=5.5 Hz, 3H), 2.07 (s, 3H), 2.62-2.79 (m, 4H), 5.15 (s, 2H), 6.87 (q, J=5.5 Hz, 1H), 7.30-7.43 (m, 5H).

Example 13(ii) Succinic Acid mono-(1-acetoxy-ethyl)ester

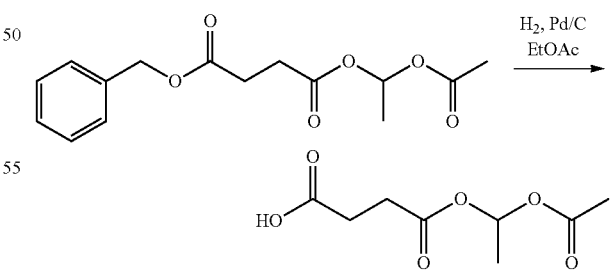

Succinic acid 1-acetoxy-ethyl ester benzyl ester (6.1 g, 20.7 mmol) was dissolved in ethyl acetate (60 mL) and 10% palladium on charcoal (160 mg) was added. The reaction was then placed under an atmosphere of hydrogen for 48 hours. The reaction was filtered through celite, and the filtrate was concentrated in vacuo. The residue was purified by MPLC eluting with a gradient from isohexane to 50% ethyl acetate:isohexane, to give the title compound (3.2 g). $^1$H NMR (CDCl$_3$, ppm) δ 1.49 (d, J=5.5 Hz, 3H), 2.09 (s, 3H), 2.61-2.76 (m, 4H), 6.89 (q, J=5.5 Hz, 1H).

Assay Protocols

Platelet Isolation

Human platelets were isolated from venous blood collected in K$_2$EDTA vials through two centrifugation steps in room temperature. After 10 min at 300 g, platelet rich plasma was collected and transferred to new vials. 5 min at 4600 g yielded a platelet pellet that was resuspended in an appropriate amount of plasma. The cell concentration was determined with a Swelab Alfa Hematocytometer (Boule Medical AB, Stockholm, Sweden).

High resolution Respirometry

Measurement of mitochondrial respiration was performed in a high-resolution oxygraph (Oxygraph—2 k, Oroboros Instruments, Innsbruck, Austria) at a constant temperature of 37° C. Platelets were suspended in the 2 mL glass chamber at a concentration of 200-400*10$^6$ cells/mL.

Screening for Potential Drug Candidates

Two screening protocols were utilized.

(1) Initial screen, complex II-effect, was performed with isolated intact platelets in a buffer containing 110 mM sucrose, HEPES 20 mM, taurine 20 mM, K-lactobionate 60 mM, MgCl$_2$ 3 mM, KH$_2$PO$_4$ 10 mM, EGTA 0.5 mM, BSA 1 g/l, pH 7.1. After baseline respiration with endogenous substrates was established, complex I was inhibited with Rotenone 2 mM. Drug candidates dissolved in DMSO were titrated in steps to 100 μM, 500 μM and 5 mM final concentration. Subsequently, cell membranes were permeabilised with digitonin (1 mg/1*10$^6$ pit). After stabilized respiration, Succinate 10 mM was added and after the respiration stabilized the experiment was terminated by addition of the complex III inhibitor Antimycin at final concentration 1 μg/mL and the residual respiration measured. FIG. 1 shows the protocol for evaluating novel cell-permeable mitochondrial substrates. In the assay, mitochondrial function in intact cells is repressed with the respiratory complex I inhibitor rotenone. Drug candidates are compared with endogenous substrates before and after permeabilization of the plasma membrane to evaluate bioenergetic enhancement or inhibition.

(2) In the second protocol, convergent respiration, the same respiration buffer and cell concentrations as described above was used. After basal respiration was established, the mitochondrial uncoupler FCCP was added at a concentration of 2 μM. Drug candidates dissolved in DMSO were titrated in steps to 100 μM, 200 μM, 400 μM, 600 μM, 1 mM, 2 mM, 5 mM and 10 mM final concentration. The concentration needed to reach maximum convergent respiration was noted. The experiment was terminated by addition of 2 μM Rotenone and 1 μg/mL Antimycin and residual respiration measured. FIG. 2 describes the protocol for evaluating the potency of novel cell-permeable mitochondrial substrates. In the assay, mitochondrial activity is stimulated by uncoupling the mitochondria with the protonophore FCCP. Drug candidates are titrated to obtain the level of maximum convergent (complex I- and complex II-derived) respiration. After rotenone addition, complex II-dependent stimulation is obtained. The complex III-inhibitor Antimycin is added to evaluate residual (mainly non-mitochondrial) oxygen consumption.

Properties of Desired Compound (1) The ideal compound stimulates respiration in rotenone-inhibited intact cells at low concentration in the CII-screening protocol without inhibitory effect on succinate stimulated respiration after permeabilization. After inhibition of respiration with mitochondrial toxins, respiration should be halted. Please refer to FIG. 1. and the listing below.

a>b means that a is greater than b a>>b means that a is much greater than b a→b means that the value of a is approaching the value of b Desired properties of compounds:

maximum value of a reached at low drug concentration.

a>>a a→b' c→c d→d'

Compounds impermeable to the cellular membrane are identified in the assay as:

a→a'

Non mitochondrial oxygen consumption induced by drug candidate is identified when d>d'

TABLE 1

Results of complex II screening assay of example compounds.

| Example No. | Mitochondrial Respiration |
|---|---|
| 1 | (+) |
| 2 | ++ |
| 3 | +++ |
| 4 | ++ |
| 5 | +++ |
| 6 | + |
| 7 | ++ |
| 8 | ++ |
| 9 | + |
| 10 | ++ |
| 11 | (+) |
| 12 | + |
| 13 | +++ |
| 14 | +++ |
| 15 | (+) |
| 16 | ++ |
| 17 | +++ |
| 18 | +++ |

Complex II-dependent respiration in screening assay (FIG. 1.) with rotenone-inhibited intact human platelets.
− no stimulation,
(+) stimulation starts at 5 mM,
+ stimulation starts at 0.5 mM and reaches maximum at 5 mM,
++ stimulation gradually increases and reaches maximum at 5 mM,
+++ stimulation gradually increases and reaches maximum at ≤0.5 mM.

(2) In the convergent respiration screening assay the ideal compound displays a higher respiration with stepwise titration compared to control in uncoupled mitochondria in intact cells. Please refer to schematic protocol in FIG. 2 and exemplifying graphs from experiments with example compounds number 3, 5 and 13 in FIG. 3. FIG. 3 shows the increase in respiration (oxygen flux per unit) with stepwise titration of drugs compared to control (disodium succinate) in intact human platelets (FIG. 2.).

A. Example compound no. 3

B. Example compound no. 5

C. Example compound no. 13

Previously Known Related Inactive Compounds

Previously described is the use of several different succinic acid esters in cellular assays. Please refer to Table 2. for screening assays results for these compounds.

TABLE 2

Results of complex II screening assay in previously known related compounds.

| Example No. | Mitochondrial Respiration |
|---|---|
| Diethyl succinate | − |
| Monomethyl succinate | − |
| Dimethyl succinate | − |

Complex II-dependent respiration in screening assay (FIG. 1.) with rotenone-inhibited intact human platelets.
− no stimulation,
(+) stimulation starts at 5 mM,
+ stimulation starts at 0.5 mM and reaches maximum at 5 mM,
++ stimulation gradually increases and reaches maximum at 5 mM,
+++ stimulation gradually increases and reaches maximum at ≤0.5 mM.

The invention claimed is:

1. A protected succinate selected from

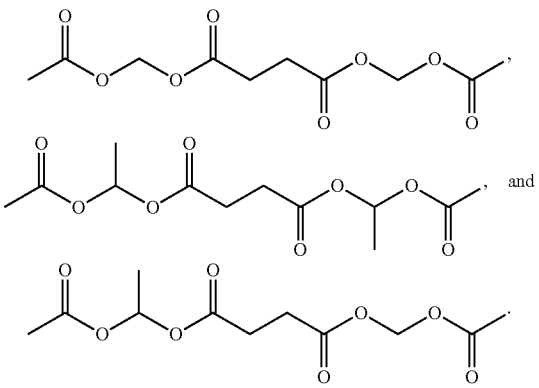

2. A composition comprising a protected succinate according to claim 1 and a pharmaceutically or cosmetically acceptable excipient.

* * * * *